US010391146B2

(12) United States Patent
King et al.

(10) Patent No.: US 10,391,146 B2
(45) Date of Patent: Aug. 27, 2019

(54) METHOD TO FUNCTIONALIZE CELLS IN HUMAN BLOOD, OTHER FLUIDS AND TISSUES USING NANOPARTICLES

(71) Applicant: Cornell University, Ithaca, NY (US)

(72) Inventors: Michael R. King, Ithaca, NY (US); Michael J. Mitchell, Ithaca, NY (US); Kuldeepsinh Rana, Lakewood, CO (US); Elizabeth C. Wayne, Ithaca, NY (US); Chris B. Schaffer, Ithaca, NY (US); Siddarth Chandrasekaran, Ithaca, NY (US)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 14/909,523

(22) PCT Filed: Aug. 4, 2014

(86) PCT No.: PCT/US2014/049602
§ 371 (c)(1),
(2) Date: Feb. 2, 2016

(87) PCT Pub. No.: WO2015/017854
PCT Pub. Date: Feb. 5, 2015

(65) Prior Publication Data

US 2016/0184395 A1 Jun. 30, 2016

Related U.S. Application Data

(60) Provisional application No. 61/861,487, filed on Aug. 2, 2013.

(51) Int. Cl.

| | |
|---|---|
| ***A61K 39/00*** | (2006.01) |
| ***A61K 38/17*** | (2006.01) |
| ***A61K 9/127*** | (2006.01) |
| ***A61K 9/00*** | (2006.01) |
| ***C07K 16/28*** | (2006.01) |
| ***A61K 47/68*** | (2017.01) |
| ***A61K 47/69*** | (2017.01) |

(52) U.S. Cl.
CPC ........ *A61K 38/1793* (2013.01); *A61K 9/0019* (2013.01); *A61K 9/127* (2013.01); *A61K 38/178* (2013.01); *A61K 47/6849* (2017.08); *A61K 47/6911* (2017.08); *A61K 47/6913* (2017.08); *C07K 16/2896* (2013.01)

(58) Field of Classification Search
None
See application file for complete search history.

(56) References Cited

U.S. PATENT DOCUMENTS

| | | | | |
|---|---|---|---|---|
| 2005/0031620 | A1* | 2/2005 | Thorpe ................ | A61K 39/395 424/155.1 |
| 2008/0095755 | A1 | 4/2008 | Kink et al. | |
| 2010/0112026 | A1 | 5/2010 | Karp et al. | |
| 2010/0183727 | A1* | 7/2010 | Iannacone .............. | A61K 39/00 424/489 |
| 2012/0189690 | A1 | 7/2012 | Anel-Bernal et al. | |

OTHER PUBLICATIONS

Chandrasekaran et al, Lab Chip 14:118-127, online published Jul. 25, 2013.*
Rana et al, Biotech and Bioengine 102: 1692-1702, 2009.*
Nimrichter et al, Blood 112:3744, 2008.*
Rana et al, Mol. Pharmaceutics 9: 2219-27, Jun. 2012, IDS #3, filed on Feb. 2, 2016.*
Mitchell, M., et al., E-Selectin Liposomal and Nanotube-Targeted Delivery of Doxorubicin to Circulating Tumor Cells, J. Control Release, Jun. 28, 2012, vol. 160, No. 3, pp. 609-617.
Kamohara, H., et al., Regulation of Tumour Necrosis Factor-Related Apoptosis-Inducing Ligand (TRAIL) and TRAIL Receptor Expression in Human Neutrophils, Immunology, Feb. 2004, vol. 111, No. 2, pp. 186-194.
Rana, K, et al., Inducing Apoptosis in Rolling Cancer Cells: A Combined Therapy With Aspirin and Immobilized TRAIN and E-Selectin, Molecular Pharmacology, Aug. 6, 2012, vol. 9, No. 8, pp. 2219-2227.
McCarthy, M., et al., Evaluating the Expression and Prognostic Value of TRAIN-R1 and TRAIL-R2 in Breast Cancer, Clinical Cancer Research, Jul. 15, 2005, vol. 11, No. 14, pp. 5188-5194.

* cited by examiner

*Primary Examiner* — Lei Yao
(74) *Attorney, Agent, or Firm* — Hodgson Russ LLP

(57) ABSTRACT

Compositions and methods for inhibiting metastatic cancer cells. The compositions comprise nanoparticles which have incorporated therein leukocyte adhesion molecules and therapeutic molecules exposed on their surface. The nanoparticles may be provided attached to leukocytes. Introduction of these compositions in to the circulation of individuals results in inhibition and reduction of metastatic cancer cells.

10 Claims, 24 Drawing Sheets

| | LIPOSOME | LIPOSOME + PROTEINS |
|---|---|---|
| PARTICLE SIZE (nm) | 112.37 +/- 1.82 | 181.50 +/- 4.5 |

METHOD TO FUNCTIONALIZE CELLS IN HUMAN BLOOD, OTHER FLUIDS AND TISSUES USING NANOPARTICLES

CROSS-REFERENCE TO RELATED APPLICATIONS

This application claims priority to U.S. Provisional Application No. 61/861,487 filed on Aug. 2, 2013, the disclosure of which is incorporated herein by reference.

STATEMENT REGARDING FEDERAL FUNDING

This invention was made with government support under grant number CA143876 awarded by the National Institutes of Health. The government has certain rights in the invention.

BACKGROUND OF THE INVENTION

Cancer metastasis is responsible for over 90% of cancer related deaths. The metastatic spread of cancer is due to the shedding of cancer cells from a primary tumor, which enters blood and lymphatic vessels as circulating tumor cells, which can then travel to anatomically distant organs to form new tumors.

Currently, there are no methods to target circulating tumor cells in the bloodstream to prevent metastasis. There are related technologies that isolate circulating tumor cells (CTC) from patient blood, which can be used to track the severity of the cancer. However, there are no related technologies that can both capture and kill rare CTC in blood and lymphatic vessels.

SUMMARY OF THE INVENTION

This disclosure provides a method to functionalize cells directly within the bloodstream using nanoparticles. In one embodiment, white blood cells are functionalized with nanoparticles which can then kill circulating tumor cells (CTC) in blood and lymphatic vessels to prevent cancer metastasis. In one embodiment, white blood cells are functionalized with nanoparticles which then adhere to various forms of cancer cells, immune cells and/or sites of inflammation.

The nanoparticle may be liposomes, silica nanoparticles, such as Cornell dots, quantum dots or any other nanoparticle that can be functionalized on its surface.

The nanoparticles functionalization can comprise functionalization with ligands, small molecules, protein, peptide, antibodies, aptamers, nucleic acids and/or chemotherapeutics or any other moiety that can be functionally attached to a nanoparticle. For example, the functionalization can comprise a moiety or molecule that recognizes white blood cells, such as selectin such that the nanoparticle functionalized with selectin binds to the selectin binding partner on the white blood cell. Another example is anti-CD57 which can bind to CD-57 which is found on NK cells. The nanoparticle can be further functionalized with another moiety or molecule that recognizes the target of interest, such as a CTC, other immune cells, sites of inflammation or cancer cells located in bone marrow or lymph nodes (such cells may be called disseminated tumor cells or DTCs).

It would be advantageous to select a moiety or molecule that recognizes a moiety or molecule specific to the target of interest. The nanoparticle can be functionalized with a molecule or moiety which induces an action specific for the target. One embodiment would be functionalization of the nanoparticle with apoptosis inducing ligands, such as TNF-related apoptosis-inducing ligand (TRAIL), which specifically binds DR4 or DR5 which are found on tumor cells and upon binding of TRAIL to the DR receptor induces apoptosis. In another embodiment, the nanoparticles are functionalized with chemotherapeutic molecules.

One example of use is to introduce a nanoparticle functionalized with selectin and TRAIL into the blood stream. The nanoparticle interacts with the white blood cell via interaction with selectin. The CTC further interacts with remaining free selectin molecules on the nanoparticle:white blood cell complex and due to close of TRAIL on the nanoparticle to the DR receptors on the CTC, the CTC receptor binds to TRAIL, inducing apoptosis/cell death of the CTC.

This invention can be used to treat highly metastatic cancers that travel through blood and lymphatic vessels, such breast, prostate, colorectal cancer, gastrointestinal tract cancers, pancreatic cancer, lung cancer and the like.

Another example of use is to introduce a nanoparticle functionalized with Selectin and an inflammation marker into the blood stream. The nanoparticle interacts with the white blood cell via Selectin. This functionalized nanoparticle:white blood cell complex further interacts with an inflammation site via moieties which bind to inflammation specific markers. The nanoparticle can then have a third functionalized moiety attached to it, or contained within it, which relieves or reduces the inflammation.

The present disclosure provides a new approach to functionalize cells in the blood using nanoparticles functionalized with different moieties and/or molecules. One moiety or molecule comprises selectin or another molecule which recognizes a host cell, such as blood cell, such as, for example, a white blood cell. An optional second moiety or molecule targets a second type of cell, such as circulating tumor cell. A last moiety or molecule binds to the second type of cell causing an action, such as cell death. In one embodiment, the cancer cells in the blood are killed by causing circulating white blood cells to present the cancer-specific apoptosis ligand TRAIL on their surface (via nanoparticles) along with E-selectin adhesion receptor. This approach occurs by using a nanoparticle functionalized with E-selectin and TRAIL. The E-selectin molecule binds to its receptor on the white blood cell. The tumor cell binds to other free E-selectin on the nanoparticle and then due to proximity, TRAIL binds to the TR receptor on the tumor cell surface.

This approach, demonstrated in vitro with human blood and also in vivo in mice, mimics both the cytotoxic activity of natural killer cells and also the chemical engineering concept of a fluidized bed reactor, which increases surface area for surface-catalyzed reactions. The resulting "unnatural killer cells" are an effective means to neutralize circulating tumor cells that enter blood with the potential to form new metastases

BRIEF DESCRIPTION OF THE FIGURES

The patent application contains at least one drawing executed in color. Copies of this patent or patent application publication with color drawing(s) will be provided by the Office upon request and payment of the necessary fee.

DETAILED DESCRIPTION OF THE INVENTION

Figure 1:
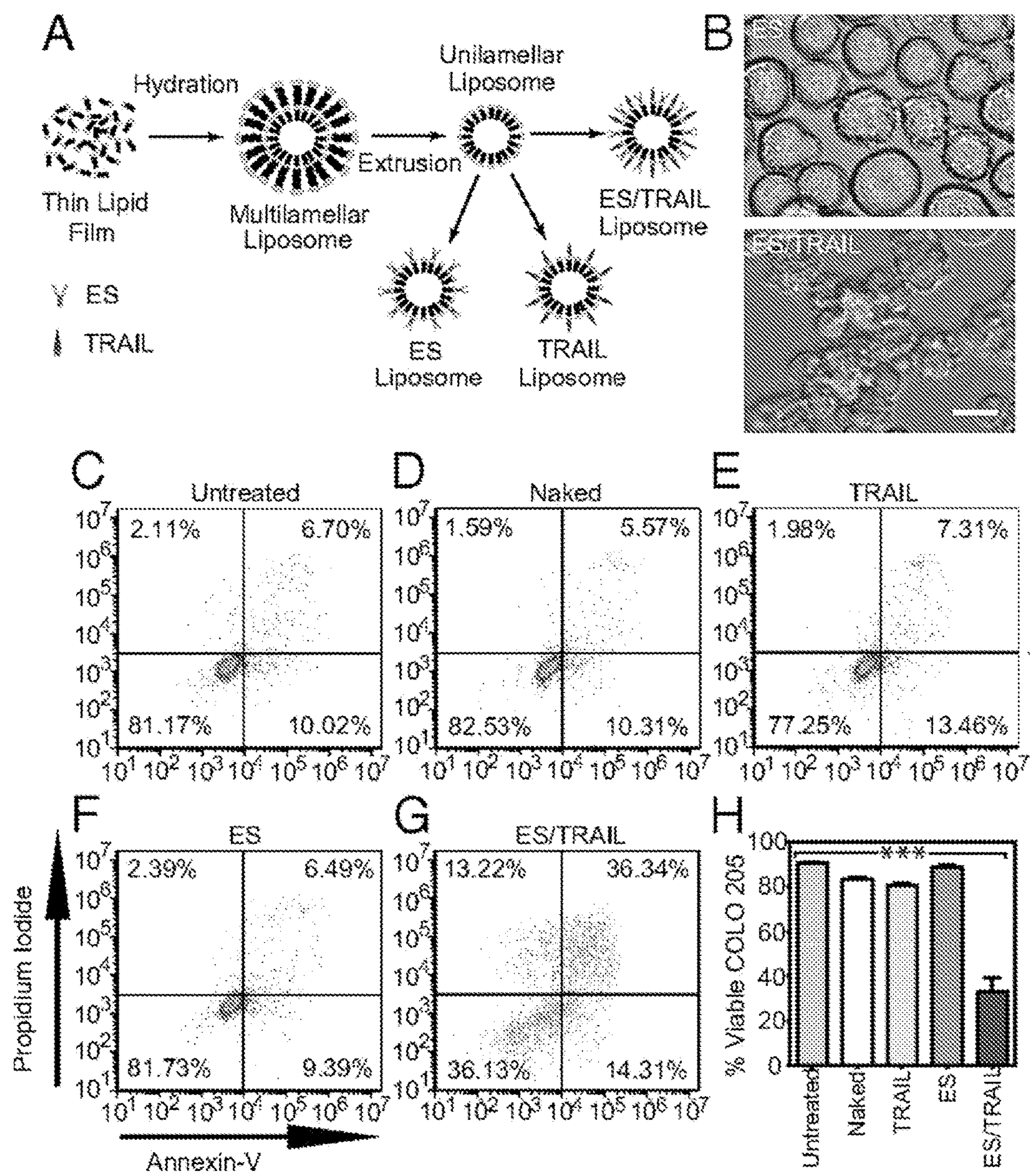
FIG. 1. ES/TRAIL liposomes adhesively interact with and kill cancer cells under uniform shear flow. (A) Synthesis of ES, TRAIL, and ES/TRAIL unilamellar liposomes using a thin film hydration method. Briefly, lipids in chloroform were dried overnight to form a thin lipid film. Lipids were then hydrated and subjected to freeze-thaw cycles to form multilamellar liposomes, which were extruded through membranes to form unilamellar liposomes. ES, TRAIL, or a combination of ES and TRAIL were then conjugated to Ni-NTA on the liposome surface. To assess the ability of ES/TRAIL liposomes to target and kill cancer cells under flow, ES/TRAIL liposomes were added to a suspension of COLO 205 cancer cells and exposed to shear flow in a cone-and-plate viscometer at a shear rate of 188 $s^{-1}$ for 2 h. Cells were then removed, washed, placed into culture for 24 h, and assessed for cell viability. (B) COLO 205 morphology after treatment with ES (top) and ES/TRAIL (bottom) liposomes under shear flow. Scale bar=20 μm. (C-G) Representative propidium iodide/Annexin-V flow cytometry plots of unsheared cancer cells (C) and cells sheared with naked (D), TRAIL-bound (E), ES-bound (F), and ES/TRAIL-bound liposomes (G) under shear flow. Cells were classified into four categories based on dye uptake: viable cells (negative for Annexin-V and propidium iodide (PI)), early apoptotic cells (positive for Annexin-V only), late apoptotic cells (positive for Annexin-V and PI) and necrotic cells (positive for PI only). (H) Percent of viable cells after treatment for each group. n=3 for all samples. Bars represent the mean±SD in each treatment group. ***P<0.0001 (one-way ANOVA with Tukey post test).

The present disclosure provides a new approach to targeting metastatic cancer cells, including circulating cancer cells and cancer cells that have spread to lymph nodes. The method of the present disclosure comprises providing tools for functionalizing host cells that naturally seek out cancer cells in vivo. Examples of such host cells include white blood cells and hematopoietic stem and progenitor cells. The host cells are functionalized via providing functionalized nanoparticles such that the functionalized host cells deliver the functionalized nanoparticles to cancer cells, and inhibit or destroy the cancer cells.

A feature of the present disclosure is that the functionalized nanoparticles do not target cancer cells directly. Rather, they use host cells (also referred to herein as intermediate cells) like leukocytes to find cancer cells. Thus, the approach makes use of intermediate cells (which normally seek out cancer cells), to facilitate delivery of the nanoparticles to them. Another feature of the disclosure is that the intermediate cells only have receptors (or complementary ligands) for the adhesion molecules and preferably do not have receptors for the therapeutic molecules. The target cells have receptors for therapeutic molecules and may have receptors for adhesion molecules. The intermediate cells seek out target cells and when armed with the nanoparticles, are able to deliver the therapeutic molecules to the target cells. In this manner, the intermediate cells can become “unnatural” killer cells.

In one embodiment, the intermediate cells are leukocytes and the adhesion molecule is selectin. In one embodiment, the intermediate cells are NK cells and the adhesion molecule is an antibody to CD57. In one embodiment, the intermediate cells are CD34+ hematopoietic stem and progenitor cells and the adhesion molecules is an antibody to CD34.

In one embodiment, this disclosure provides nanoparticles comprising both an adhesion molecule and a therapeutic molecule. In one embodiment, the adhesion molecule is one by which the nanoparticles can attach to leukocytes. The therapeutic molecule is one which will attach and/or inhibit or kill target cells—such as cancer cells. In one embodiment, when the nanoparticle is a liposome, the adhesion molecule and the therapeutic molecules are incorporated into the bilayer of the liposome such that they are exposed to the exterior and are available for interaction with other cells. For example, the selectin or the anti-CD57 molecules on liposomes are available for attachment to their corresponding ligands on leukocytes, and the TRAIL molecules are available for inhibiting or killing cancer cells.

In one embodiment, the present disclosure provides nanoparticles on to whose surface is incorporated i) an adhesion molecule which will attach the nanoparticles to intermediate cells; and ii) a therapeutic molecule which causes apoptosis of cells upon binding to cells displaying receptors for the therapeutic molecules.

Examples of nanoparticles are liposomal particles, silica nanoparticles, such as Cornell dots, quantum dots or any other nanoparticle that can be functionalized on its surface including PLGA or nanotubes, including carbon nanotubes and halloysite nanotubes. The nanoparticles may be liposomal which may be unilamellar or multilamellar or micelles. In one embodiment, the nanoparticles are unilamellar liposomes. In one embodiments, the nanoparticles are PLGA or nanotubes. The phospholipids making up the liposomes may be neutral or charged. For example, the phospholipids may be phosphatidyl choline, phosphatidyl ethanolamine, phosphatidyl serine or any other phospholipid. In one embodiment, the liposomes may comprise phosphatidylcholine, phosphoethanolamine, and cholesterol.

The size of the nanoparticles should be such that they are easily deliverable via the circulation. In one embodiment, the size of a majority of the nanoparticles is from 50-250 microns and all integers therebetween and all ranges therebetween. In one embodiment, the size of majority of the nanoparticles is from 100-150 microns. In one embodiment, the size of 60, 70, 80, 90, 95, 96, 97, 98, 99, or 100% of the particles is from 50-250 microns or 100-150 microns.

The number of adhesion molecules and therapeutic molecules on the nanoparticles (such as liposomes) may vary so long as attachment to host cells and then to cancer cells is achieved. For example, adhesion molecules may be more, less, or the same number as therapeutic molecules on a nanoparticle. In one embodiment, the therapeutic molecules are more than adhesion molecules. In one embodiment, the therapeutic molecules are 1×, 2×, 3×, 4×, 5×, 6×, 7×, 8×, 9× or 10× times the number of adhesion molecules on a nanoparticle. In one embodiment, the adhesion molecules are 2×, 3×, 4×, 5×, 6×, 7×, 8×, 9× or 10× times the therapeutic molecules on a nanoparticle. In one embodiment, the ratio of TRAIL molecules to selectin molecules is 1:1, 2:1, 3:1, 4:1, 5:1, 6:1, 7:1, 8:1, 9:1 or 10:1 on a nanoparticle (such as a liposome).

Adhesion molecules useful in the present disclosure are those by which the nanoparticles can attach to leukocytes under the shear stress that is experienced in the circulation into which they are introduced, such as, for example, the blood stream. Examples of such adhesion molecules include selectins such as P-selectin and E-selectin, wherein the complementary ligand on the leukocytes is selectin-binding carbohydrate ligand. Other examples of selectins include L-selectin as well as recombinant selectin molecules such as P-selectin-IgG chimera and E-selectin-IgG chimera. In one embodiment, the adhesion molecules bind only to leukocytes and cancer cells and not to non-cancer cells (other than leukocytes). The shear flow typically encountered in vivo is in the range of 50-2500 l/s. Thus, the adhesion molecules on the nanoparticles and the complimentary ligands on leukocytes should be able to provide attachment under shear stress in the range of 50-2500 $s^{-1}$ (0.5 to 25 dynes/$cm^2$ and all integers and values to the tenth decimal place therebetween) and all integers therebetween. In one embodiment, the adhesion molecules are able to provide adhesion under shear stress encountered in post-capillary venules. The range of such shear stress is 0.5-5 dynes/$cm^2$ Examples of other cell adhesion molecules include selectins, cadherins, integrins, ICAM and VCAM1 or antibodies. An advantage of using selectins is that in contrast to nanoparticles functionalized with antibodies directed to ligands on tumor cells, nanoparticles functionalized with adhesion molecules, such as selectins, form bonds that break under shear flow encountered in the circulation so that the nanoparticles do not aggregate in the circulation. Even though weak, the binding of selectin to its ligand on leukocytes appears to be accentuated by shear flow as little or no binding was observed under static conditions. This was a surprising finding.

In one embodiment, the adhesion molecule is an antibody that binds to a ligand expressed on the surface of a cancer cell. For example, the adhesion molecule may be an antibody directed to CD57. Another example of a useful antibody is an antibody directed to CD34. Other useful antibodies may be against surface markers expressed by subpopulations of blood cells, lymphocyte markers, platelet markers, monocyte markers etc. The antibodies may be monoclonal or polyclonal or may be antigen (ligand) binding fragments of the antibodies. Additionally, the antibodies may be chimeric or humanized antibodies. Such antibodies can be made by methods known in the art or are commercially available.

Examples of therapeutic molecules are those which effect apoptosis in target cells such as cancer cells. In one embodiment, the therapeutic molecule are apoptosis inducing ligands. For example, the therapeutic molecule may be tumor necrosis factor (TNF)-related apoptosis inducing ligand (TRAIL), which binds to death receptors 4 and 5 on the surface of cancer cells to induce apoptosis through the intrinsic and extrinsic pathways. In one embodiment, the therapeutic molecules are Fas ligand, TNF-alpha, or fragments of these ligands or fragments of TRAIL protein and its variants, and antibodies to these ligands, such as Fas antibody.

The liposomes may be conjugated to selectin and TRAIL by routine conjugation methods. The proteins may be attached covalently or non-covalently. In one embodiment, Ni chelating lipids like DOGS—Ni-NTA or other chemistries like avidin/biotin can be used. Other nanoparticles, such as silica nanoparticles and C-dots, may be functionalized in methods known in the art for such nanoparticles. In one embodiment, DOGS-Ni-NTA is utilized to conjugate ES and TRAIL to the liposome surface. In one embodiment, 8-12% weight percent of DOGS-Ni-NTA may be used to conjugate ES and TRAIL to the liposome surface. In one embodiment, PC, SM, cholesterol and DOGS NTA-Ni is used. In one embodiment, the amounts of each component may vary from 45-65, 25-35, 5-15 and 0.5 to 10 wt % respectively, and all values to the tenth decimal place between these values and all ranges between these values.

In one embodiment, this disclosure provides leukocytes which have been functionalized by attachment to nanoparticles, which nanoparticles are attached to the leukocytes at least via the adhesion molecules and also display therapeutic molecules (such as TRAIL) on their surface. The leukocytes may be obtained from the blood of an individual and functionalized by incubation with the nanoparticles. The leukocytes may be of one or more types. For example, the leukocytes may be natural killer cells (NK cells). In one embodiment, the leukocytes express CD3, CD14, CD16, CD19, and/or CD56.

In one aspect, the present disclosure provides compositions comprising functionalized nanoparticles, leukocytes, or both in pharmaceutically acceptable carrier suitable for administration to an individual. Such carriers are known in the art and may include, for example, normal saline, water, buffered water, isotonic aqueous solutions, glycine solutions and the like. The pharmaceutical carriers may include glycoproteins for enhanced stability, including albumin, lipoprotein and globulin. These compositions are generally sterilized by conventional means. For example, unilamellar liposomes may be sterilized using sterile filtration techniques.

In one aspect, this disclosure provides methods for targeting and killing metastatic cells, including circulating cancer cells. The method comprises introducing into the circulation of an individual who has been diagnosed with cancer or who is in need of treatment, a composition comprising the functionalized nanoparticles and/or functionalized leukocytes as described herein. The compositions may be introduced into the blood circulation and/or into the lymph circulation. The compositions may also be introduced into localized areas (at or near tumors) such that the functionalized nanoparticles or leukocytes will find their way to surrounding lymph nodes such as the draining lymph nodes.

In one embodiment, the disclosure provides a method for inhibiting metastatic cancer cells comprising introducing into the circulation of an individual a composition comprising nanoparticles which have incorporated therein or thereon leukocyte attachment molecules and cancer therapeutic molecules such that the molecules are exposed on the surface and available for interaction with leukocytes and cancer cells, wherein introduction of the nanoparticles into the circulation of an individual results in reduction in the number of metastatic cancer cells.

In one embodiment, the present disclosure provides a method of killing metastatic cancer cells that are residing in a lymph node comprising a) providing nanoparticles (such as liposomes) which are functionalized with adhesion molecules (such as selectins or anti-CD-57) and therapeutic molecules (such as TRAIL), and b) introducing the nanoparticles into the lymph circulation near the lymph node of an individual. The adhesion molecules attach the nanoparticles to intermediate host cells (such as NK cells) in circulation near the lymph node. The intermediate cells do not have receptors for therapeutic molecules. The nanoparticles attach to the intermediate cells and the intermediate cells seek out cancer cells thereby causing the nanoparticles to attach to the cancer cells residing in the lymph node via the therapeutic molecules causing cell death of the cancer cells in the lymph node.

In one embodiment, the method comprises isolating leukocytes from an individual, optionally, fractionating those to select one or more types of leukocytes, functionalize the leukocytes by incubating with nanoparticles that have incorporated therein adhesion molecules and therapeutic molecules, and then administering the functionalized leukocytes back to the individual. The source of the leukocyte and the recipient of functionalized leukocytes may be the same individual or may be different individuals. If different individuals, they may be matched for compatibility for transfer of blood cells.

In one embodiment, this disclosure provides a method for inhibiting metastatic cancer cells comprising: a) obtaining leukocyte from in individual; b) contacting said leukocytes with liposomes having a leukocyte attachment molecules, such as selectin molecules, and TRAIL molecules incorporated into their bilayers or onto their surface such that the liposomes attach to the leukocytes via the leukocyte attachment molecules resulting in functionalized leukocytes; and c) introducing the functionalized leukocytes into an individual. This results in a reduction in the number of metastatic cancer cells.

While the compositions of the present disclosure may be administered any time during treatment, to optimize the effect, the compositions may be administered when the CTCs are considered to be in greater numbers in the circulation. For example, the compositions may be administered 20-30 minutes after surgical removal of a tumor. The compositions may also be given prophylactically, such as 20-30 minutes before a surgical procedure to remove a tumor. In other embodiments, the compositions may be administered multiple times in a day or on a daily basis or as needed.

In one embodiment, we provide a therapeutic approach to target and kill circulating cancer cells in the bloodstream by administration of nanoparticles functionalized with the apoptosis-inducing ligand TRAIL and the adhesion receptor selectin. The nanoparticles then functionalize leukocytes directly within blood under shear flow. The functionalization of leukocytes under flow, effectively creating a form of "unnatural killer cells" within the bloodstream, is shown to be highly effective at treating circulating cancer cells in flowing human blood in vitro, and in the peripheral circulation of mice in vivo. By the method of the present disclosure, leukocytes are used to treat CTCs directly within the bloodstream.

In one aspect, this disclosure provides a method for inhibiting circulating cancer cells comprising introducing into the circulation of an individual a composition comprising nanoparticles which have leukocyte adhesion molecules and therapeutic molecules attached thereto, wherein introduction of the nanoparticles into the individual results in targeting and reduction in the number of circulating cancer cells in the bloodstream of the individual.

The method of the present disclosure provides an approach in which, it is considered that leukocytes are functionalized via interaction with the adhesion molecules on nanoparticles and can be used to target and kill circulating cancer cells. Thus, the functionalized leukocytes act as mimics of the cytotoxic activity of natural killer (NK) cells. The resulting "unnatural killer cells" provide an effective means to neutralize circulating tumor cells that enter blood with the potential to form new metastases.

In one embodiment, the method comprises targeting and killing cancer cells in the bloodstream, in which the extensive surface area of circulating leukocytes is used to display the cancer-specific apoptosis ligand TRAIL and selectin adhesion receptor to the surrounding fluid. The approach is inspired by the cytotoxic activity of natural killer cells, and is effective at killing cancer cells both in in vitro human blood samples and in mouse blood circulation. The mechanism is surprising and unexpected in that this repurposing of leukocytes in flowing blood is more effective than directly targeting the cancer cells with liposomes or soluble protein.

The compositions and methods of the present disclosure are useful for any indication where specific targeting of cells is helpful. For example, the compositions and methods are useful in any type of cancer. In one embodiment, the cancer often results in dissemination of cancer cells from its primary site, and such cells may appear as circulating cancer cells. Or the cells may lodge themselves in lymph nodes near the primary site or in some cases far from it. Examples of cancer include breast, prostate, lung cancer, melanoma, pancreatic, colorectal, GI tract, retinoblastoma, bladder and any other type of cancer.

The present method may be combined with the administration of agents known to sensitize cancer cells to TRAIL-mediated apoptosis, including conventional chemotherapeutics (camptothecin, cisplatin, doxorubicin, 5-fluorouracil, irinotecan, paclitaxel, gemcitabine), proteasome inhibitors, Bcl-2 inhibitors, IAP antagonists, HDAC inhibitors, CD20 antibodies, irradiation, synthetic triterpenolds, Sorafenib, aspirin, and natural products such as curcumin and piperlongumine. Thus, in one embodiment, the method comprises administration of the nanoparticles disclosed herein to an individual in need of treatment (such as in individual who is considered to be at risk of having circulating cancer cells) and administration of an agent that sensitizes cancer cells to apoptosis inducer (such as TRAIL). The agent sensitizing cancer cells to apoptosis inducers may be given before, after, or at the same time as the nanoparticles.

In the following description, reference is made to the accompanying drawings that form a part hereof, and in which is shown by way of illustration specific embodiments which may be practiced. These embodiments are described in detail to enable those skilled in the art to practice the invention, and it is to be understood that other embodiments may be utilized and that structural and logical changes may be made without departing from the scope of the present invention. The following description of example embodiments is, therefore, not to be taken in a limited sense, and the scope of the present invention is defined by the appended claims.

The Abstract is provided to comply with 37 C.F.R. § 1.72(b) to allow the reader to quickly ascertain the nature and gist of the technical disclosure. The Abstract is submitted with the understanding that it will not be used to interpret or limit the scope or meaning of the claims.

Example 1

This example describes the use of nanoparticles functionalized with cancer-specific apoptosis ligand TRAIL and selectin molecules to target and kill colon and prostate cancer cells in the blood. This approach, is demonstrated in vitro with human blood and also in mice.

Materials and Methods

Reagents and antibodies. Human serum albumin (HSA), bovine serum albumin (BSA), Accutase™, HEPES, DMSO, NaCl, $MgCl_2$, $CaCO_3$ and chloroform (ACS grade with 0.5-1% ethanol added as stabilizer) were all obtained from Sigma-Aldrich (St Louis, Mo.). RPMI 1640 cell culture media, fetal bovine serum (FBS), Hank's balanced salt solution (HESS), penicillin-streptomycin (PenStrep) and Dulbecco's phosphate buffered saline (DPBS) were all obtained from Invitrogen (Grand Island, N.Y.). His-tagged recombinant human tumor necrosis factor-related apoptosis-inducing ligand (TRAIL), his-tagged recombinant human E-selectin-IgG chimera (ES) and Annexin-V FITC Apoptosis Detection Kit were purchased from R&D Systems (Minneapolis, Minn.). BCECF AM solution and trypsin-EDTA solution were obtained from Invitrogen (Carlsbad, Calif.). PBS-based enzyme-free cell dissociation media was purchased from Millipore (Billerica, Mass.). L-α-lysophosphatidylcholine from egg (Egg PC), sphingomyelin from egg (Egg SM), ovine wool cholesterol (Chol), 1,2-dioleoyl-sn-glycero-3-[(N-(5-amino-1-carboxypentyl) iminodiacetic acid) succinyl] (nickel salt) (DOGS NTA-Ni) and 23-(dipyrrometheneboron difluoride)-24-norcholesterol (Bdp-Chol, Ex/Em 490 nm/504 nm) either dissolved in chloroform (Egg PC, Egg SM, Chol, DOGS NTA-Ni) or in powder form (Bdp-Chol) were purchased from Avanti Polar Lipids (Alabaster, Ala.). Rat anti-human CD62E (E-selectin) antibody was purchased from Abcam (Cambridge, Mass.). Anti human CD3, CD14, CD16, CD19 and CD56 conjugated with Pacific Blue™, APC Cy7™, PERCP-Cy5.5, APC, and PE respectively along with corresponding isotypes were all purchased from BD Biosciences (San Jose, Calif.).

Cell lines and cell culture. Colon cancer cell line COLO 205 (ATCC number CCL-222) was obtained from ATCC (Manassas, Va.) and cultured in RPMI 1640 supplemented with 2 mM L-Glutamine, 25 mM HEPES, 10% v/v FBS and 100 U/mL PenStrep (complete media) under humidified conditions at 37° C. and 5% $CO_2$. Prostate cancer cell line PC-3 (ATCC number CRL-1435) was obtained from ATCC and cultured in F-12K medium supplemented with 10% v/v FBS and 100 U/mL PenStrep. Human umbilical vein endothelial cells (HUVEC) were purchased from Cascade Biologics (Portland, Oreg.) and maintained in Medium 200 (Cascade Biologics) supplemented with low-serum growth supplement (Cascade Biologics) and 5% fetal bovine serum (Invitrogen). HUVECs were utilized from passages 2-5 for experiments. For all experiments, >95% viability was assessed by trypan blue exclusion dye.

Preparation of liposomes. Multilamellar liposomes, composed of egg L-α-lysophosphatidylcholine (Egg PC), egg sphingomyelin (Egg SM), ovine wool cholesterol (Chol), 1,2-dioleoyl-sn-glycero-3-[(N-(5-amino-1-carboxypentyl) iminodiacetic acid) succinyl] (nickel salt) (DOGS NTA-Ni) at weight ratios 60-50%:30%:10%:0-10% (Egg PC/Egg SM/Chol/DOGS NTA-Ni), were prepared by a thin lipid film method. DOGS-NTA-Ni is a lipid conjugated to nickel-nitrilotriacetic acid (Ni-NTA) that allows for attachment to his-tagged proteins. Briefly, stock solutions of all lipids were prepared by dissolving powdered lipids in chloroform to produce a final concentration of 5 mg/mL Egg PC, 20 mg/mL Egg SM, 5 mg/mL Chol and 20 mg/mL DOGS-NTA-Ni in glass containers and stored at −20° C. Appropriate volumes of the lipids were taken from the stock solution to make lipids with varying concentrations of DOGS NTA-Ni in a glass tube and gently dried under nitrogen. To ensure complete removal of chloroform, the lipids were left under vacuum for an additional 12 h. With increasing amounts of DOGS NTA-Ni, the corresponding amount of Egg PC was decreased (Table S1). The lipid film was hydrated with a liposome buffer composed of 150 mM NaCl, 10 mM HEPES and 1 mM $MgCl_2$ dissolved in nuclease-free water to create multilamellar liposomes. The resulting multilamellar liposomes were sized by repeated thawing and freezing, and then subjected to 15 extrusion cycles at 60° C. through two different pore size (200 and 100 nm) polycarbonate membranes (Nucleopore, Whatman, N.J., USA) to produce unilamellar nanoscale liposomes. Recombinant human ES and TRAIL were dissolved in nuclease-free sterile water to a final concentration of 1 mg/mL and 100 μg/mL. Aliquots of stock solutions were stored at −20° C. and used as needed within 60 days. Freshly prepared nanoscale liposomes were then incubated with ES (final concentration 71.43 nM) and TRAIL (250 nM final concentration) for 30 min at 37° C. and then overnight at 4° C., to ensure maximum protein binding via the interaction between his-tag and Ni-NTA. Based on approximations for ligand density on liposomes suggested in previous work by Huang and Mason (1), there were approximately 65 TRAIL and 19 E-selectin proteins present on the surface of each liposome, assuming a unilamellar liposome diameter of 100 nm. To remove unbound TRAIL and ES, liposomes were diluted 1:6 with liposome buffer and subjected to ultracentrifugation at 100000 g for 3 h at 4° C. The supernatant with unbound TRAIL and ES was carefully removed and collected for further evaluation, and the remaining liposomes were gently resuspended in buffer. A similar procedure was used to create fluorescent conjugated liposomes by replacing ovine wool cholesterol with 23-(dipyrrometheneboron difluoride)-24-norcholesterol. Freshly prepared nanoscale liposomes were diluted in buffer, and the mean particle diameter and surface charge (zeta potential) were measured by dynamic light scattering using a Malvern Zetasizer nano ZS (Malvern Instruments Ltd., Worcestershire, UK), according to the manufacturer's protocols. Conjugated liposomes were measured to be 117.8±10.3 nm in diameter, with a zeta potential of −5.7±4.6 mV.

Static experiments. COLO 205 cells were seeded in multiwell plates at a seeding density of 300,000 cells/mL, 1 day prior to experimentation to ensure that the cells were in the linear phase of the growth cycle. Media was changed prior to experimentation. Cells were incubated with either the supernatant from ultracentrifugation or 10 μL of conjugated and purified liposomes. The cells were maintained in culture conditions with the supernatant or nanoscale lipids for 24 h and later analyzed by an Annexin-V assay to quantify the proportion of viable cells.

Uniform shear flow experiments. To simulate the shear stress conditions of blood flow, cancer cells were subjected to uniform shear in a cone-and-plate viscometer. Cancer cells seeded one day prior to the experiment were gently detached from the surface using PBS-based enzyme-free cell detachment solution or accutase. Cells were then washed twice in 1×DPBS and resuspended in buffer at a concentration of $1\times10^6$ cells/mL. 10 μL of lipids was added to 490 μL of cell suspension (at $10^6$ cells/mL) and immediately added to the cone-and-plate viscometer. Shear rate was set to 188 $s^{-1}$ for 2 h. All samples were exposed to shear flow at RT, to prevent potential sample evaporation and/or drying in the cone-and-plate viscometer over prolonged periods of shear. After 2 h, the cells were removed and washed twice in resuspension buffer at 200 g for 5 min. Cells were resuspended in complete media and cultured for 24 h. In the case of fluorescent lipids, an aliquot was taken for visual inspection on an inverted microscope (Olympus America Inc, Melville, N.Y.) equipped with fluorescence and an intensified CCD digital camera (Cooke Corporation, Romulus, Mich.) to record images. For spiking experiments, peripheral blood was collected into Vacutainer tubes containing heparin and allowed to equilibrate to RT before use. $1\times10^6$ COLO 205 or PC-3 cells were tagged fluorescently with 3 μM BCECF AM solution for 15 min at 37° C., washed twice and collected via centrifugation at 200 g for 5 min. The supernatant was discarded, and the collected cells were resuspended in 1 mL of whole blood. 10 μL of lipid was then added to 490 μL of spiked blood and immediately added to a cone-and-plate viscometer previously coated with 5% BSA. Spiked blood was subjected to a uniform shear rate of 188 $s^{-1}$ for 2 h. As an additional comparison for spiking experiments, identical experiments were performed in buffer instead of whole blood. In leukocyte functionalization experiments, 10 μL of lipid was added to 490 μL human blood, sheared in a cone-and-plate viscometer at a uniform shear rate of 188 $s^{-1}$ for 2 h, and subsequently centrifuged to remove the plasma containing unbound liposomes. The removed plasma was replaced with freshly isolated plasma, and the blood samples were used for identical spiking experiments mentioned above. After shearing, the blood sample was collected from the device and carefully layered over 1.5 mL of Ficoll and centrifuged at 480 g for 50 min at RT. The buffy coat containing MNCs and cancer cells was recovered and washed twice in resuspension buffer, collected, cultured for 24 h, and analyzed for viable fluorescent cancer cells using flow cytometry. To evaluate the effect of hematocrit, the number of RBCs was varied by removal via centrifugation. Volumes of RBCs were replaced with excess plasma from the same blood donor. Cancer cells were spiked into blood samples as mentioned earlier, at a concentration of $1\times10^6$ cells/mL. 10 μL of liposome solution was added to 490 μL of blood and sheared for 2 h at 188 $s^{-1}$. Samples were collected, incubated, and analyzed for viability on a flow cytometer as described above. In some experiments, 490 μL of whole blood was sheared with 10 μL of liposome solution, and the plasma and any remaining unbound liposomes and/or liposome fragments were separated by centrifugation. To determine the effects of remaining unbound liposomes and/or liposome fragments on cancer cell viability, the recovered plasma was incubated with 500,000 COLO 205 cells for 24 h at 37° C. and analyzed for cell viability using flow cytometry.

Polymorphonuclear (PMN) and mononuclear cell (MNC) isolation. All human subject protocols were approved by the Institutional Review Board for Human Participants of Cornell University. Peripheral blood was collected from healthy, willing donors after informed consent into Vacutainer tubes containing heparin and allowed to equilibrate at room temperature (RT) before use. 3 mL of blood diluted with resuspension buffer was carefully layered over 3 mL of 1-Step™ Polymorphs (Accurate Chemical & Scientific Corporation, Westbury, N.Y.) and centrifuged at 480 g for 50 min at RT. Two separate layers of MNCs and PMNs were collected and washed twice with resuspension buffer.

Leukocyte functionalization with ES/TRAIL liposomes in whole blood. To assess the adhesion of ES/TRAIL liposomes to leukocytes in whole blood under flow, 490 μL of whole blood was sheared with 10 μL of fluorescent ES/TRAIL liposome solution for 30 min in a cone-and-plate viscometer at a shear rate of 188 $s^{-1}$. Leukocytes were then separated using 1-Step™ Polymorphs and assessed for adherent ES/TRAIL liposomes using confocal microscopy. To assess the fraction of leukocyte subpopulations that adhere to ES/TRAIL liposomes, leukocytes were labeled with anti-human CD3, CD14, CD16, CD19 and CD56, along with corresponding isotype controls, and analyzed for adherent ES/TRAIL liposomes using flow cytometry. To assess the specificity of the ES interaction with leukocytes, liposomes were incubated with a functional blocking anti-human E-selectin antibody prior to shearing in whole blood. To assess the fraction of leukocytes in blood adhered to ES/TRAIL liposomes before shear, fluorescent ES/TRAIL liposomes were added to whole blood and then separated using 1-Step™ Polymorphs.

Endothelial cell viability assay. 40 mm diameter circular glass coverslips (Thermo Scientific, Waltham, Mass.) were plasma treated (Harrick Plasma Cleaner, Ossining, N.Y.) for 2 min and subsequently incubated in 1% polyethylenemine (PEI) at room temperature for 10 min. Coverslips were then washed in water 3 times and treated with 0.1% glutaraldehyde (Sigma-Aldrich, St. Louis, Mo.) in PBS at room temperature for 30 min Coverslips were washed in water 3 times, dried, and treated with 0.1 mg/mL of type I rat-tail collagen (Becton Dickinson, Franklin Lakes, N.J.) in HEPES (pH 8.0, Sigma-Aldrich, St. Louis, Mo.) for 2 h at 4° C. Coverslips were placed in petri dishes (60 mm×15 mm; Sigma-Aldrich), washed 3 times in PBS, and briefly sterilized via UV exposure for 15 min. HUVECs were plated on coverslips, at a density of 500,000 cells per coverslip, in Medium 200 supplemented with low-serum growth supplement (Cascade Biologics), 5% fetal bovine serum (Invitrogen), and 100 U/mL PenStrep. HUVECs were cultured for 4 days on coverslips prior to experiments, and then adhered to the plate of a cone-and-plate viscometer using vacuum grease. HUVECs were then treated with 2.94 mL of human blood and 60 μL of PBS, ES/TRAIL (TRAIL final concentration: 0.3 μg/mL), or soluble TRAIL in PBS (TRAIL final concentration: 0.3 μg/mL) for 4 h at 37° C. in a humidified cone-and-plate viscometer at a shear rate of 188 $s^{-1}$. As a positive control, HUVECs were treated with a high concentration of soluble TRAIL (15 μg/mL). Coverslips were removed from the viscometer, gently washed in PBS, and placed in Medium 200 supplemented with low-serum growth supplement, 5% fetal bovine serum (Invitrogen), and 100 U/mL PenStrep. HUVEC morphology was assessed using brightfield and phase contrast microscopy. HUVECs were immediately placed into culture for 8 h, maintained at 37° C. and 5% $CO_2$. HUVECs were then treated with 0.25% Trypsin-EDTA solution (Gibco) for 2 min at 37° C., followed by treatment with an equal volume of trypsin neutralizer solution (Gibco). HUVECs were collected from coverslips, washed twice in PBS, and assessed for viability using an Annexin-V assay.

Liposome and COLO 205 cell injection in mice. C57BL/6J mice aged 16-20 weeks (both sexes), weighing 25-32 g, were obtained from The Jackson Laboratory. Mice were anesthetized using isoflurane (5%) for all procedures. Either 120 μL of saline, sTRAIL (15 μg/mL; TRAIL plasma concentration ~1.0 μg/mL), ES/TRAIL (TRAIL injection concentration: 15 μg/mL; TRAIL plasma concentration ~1.0 μg/mL) liposomes or ES liposomes suspended in saline were injected retro-orbitally using a 30-G needle and animals were removed from anesthesia. Three mice were used in each group. Thirty minutes later, animals were re-anesthetized and ~$2\times10^6$ COLO 205 cells, labeled by 2 μg/mL Hoescht (#H1399, Invitrogen) or 3 μM BCECF AM suspended in saline were injected into the tail vein Animals were removed from anesthesia and the cancer cells were allowed to circulate for 2 h. All animal procedures were approved by the Cornell University Institutional Animal Care and Use Committee.

Analysis of circulating COLO 205 cells Animals were euthanized with a lethal dose of pentobarbital. Blood was removed from the heart via cardiac puncture and collected into sodium heparin-coated tubes. Leukocytes and circulating COLO 205 cells were separated using Ficoll-Paque PLUS™. After centrifugation, the MNC buffy coat was collected, washed in buffer containing $Ca^{2+}$ and cultured for 2-3 h in multiwell plates. Cell viability was assessed using flow cytometry.

Two-photon imaging of lung tissue. Animals were anesthetized and received injections of saline, sTRAIL, ES/TRAIL liposomes or ES liposomes, followed by an injection of Hoescht-labeled cancer cells, as described above. After two hours of cancer cell circulation, an Alexa Fluor 568 labeled Annexin-V probe (#A13202, Invitrogen) was injected retro-orbitally and allowed to circulate for 2 h to ensure maximum detection of apoptotic cells. Animals were then given a lethal dose of pentobarbital. After euthanasia, intact lungs were resected and immediately imaged via two-photon excited fluorescence microscopy. Two-photon imaging was conducted on a locally-designed microscope using a train of 800-nm, 87-MHz, 100-fs pulses from a Ti:sapphire laser oscillator (MIRA HP, pumped by a Verdi-V18, Coherent) for excitation. Laser scanning and data acquisition were controlled by ScanImage software. For high-resolution imaging of COLO 205 Hoechst-labeled nuclei and Annexin V labeling a 20× (numerical aperture: 0.95) water-immersion objective (Olympus) was used. Fluorescence was detected using emission filters with 460-nm and 645-nm center wavelength with 65-nm bandwidth to image Hoescht and Alexa Fluor 568 (Invitrogen), respectively. Spectrally-broad autofluorescence from the lung tissue was visible in both channels.

Counting and viability scoring of COLO 205 cells in lung. Hoechst-labeled COLO 205 cells were manually counted from ~10 representative two-photon image stacks taken from the lung in each mouse using Image J (NIH) cell counting software. The Hoechst signal was of similar magnitude to the background lung autofluorescence in the 460-nm channel. To aid in identifying nuclei, the Hoechst channel was compared with the 645-nm channel, where autofluorescence was also visible, but Hoescht was not and Alexa Fluor 568 signal was significantly brighter than autofluorescence. In addition, attributes such as size and shape to distinguish the labeled COLO 205 cells were used. Each imaged volume was about 0.022 $mm^3$. The total number of cells in the lung was estimated by scaling the imaged volumes to the total lung volume, which was measured via a volume displacement method. Counts were recorded by two different observers, each blinded to the treatment received, and averaged. To determine which COLO 205 cells were apoptotic, we determined whether Alexa Fluor 568 Annexin V labeling was present at each of the COLO 205 cell nuclei we identified.

Flow cytometry. Mode of cell death was analyzed using an Annexin-V apoptosis assay on an Accuri C6 flow cytometer. Samples were prepared for as per the manufacturer's instructions. Briefly, cells were classified into four categories based on dye uptake: viable cells (negative for Annexin-V and propidium iodide (PI)), early apoptotic cells (positive for Annexin-V only), late apoptotic cells (positive for Annexin-V and PI) and necrotic cells (positive for PI only). For blood spiking experiments, fluorescent untreated cancer cells and liposome treated samples were assessed for viability using a flow cytometer. A gate was set based on a viable, untreated cancer cell control. Equal volumes from all samples were used for analysis. Cell viability was determined by measuring the amount of cells positive for fluorescent BCECF staining. For in vivo animal experiments, 100 μL of each sample was processed. A gate denoting viable, BCECF AM-labeled cancer cells was established by processing a viable, fluorescent sample of COLO 205 cells in buffer. COLO 205 cells recovered from mouse blood were differentiated based on size and fluorescence using flow cytometry. The number of cancer cells per milliliter of mouse blood was determined based on the amount of mouse blood recovered from each animal.

Statistical analysis. Where appropriate, student's t-test and one-way ANOVA with Tukey post test comparing all means were employed at a significance level of $\alpha$=0.05. All statistical analyses were performed using GraphPad Prism 5.0c for Mac OS X GraphPad software (San Diego, Calif. USA) and Kaleidagraph (Synergy) software.

Results

Figure 7:
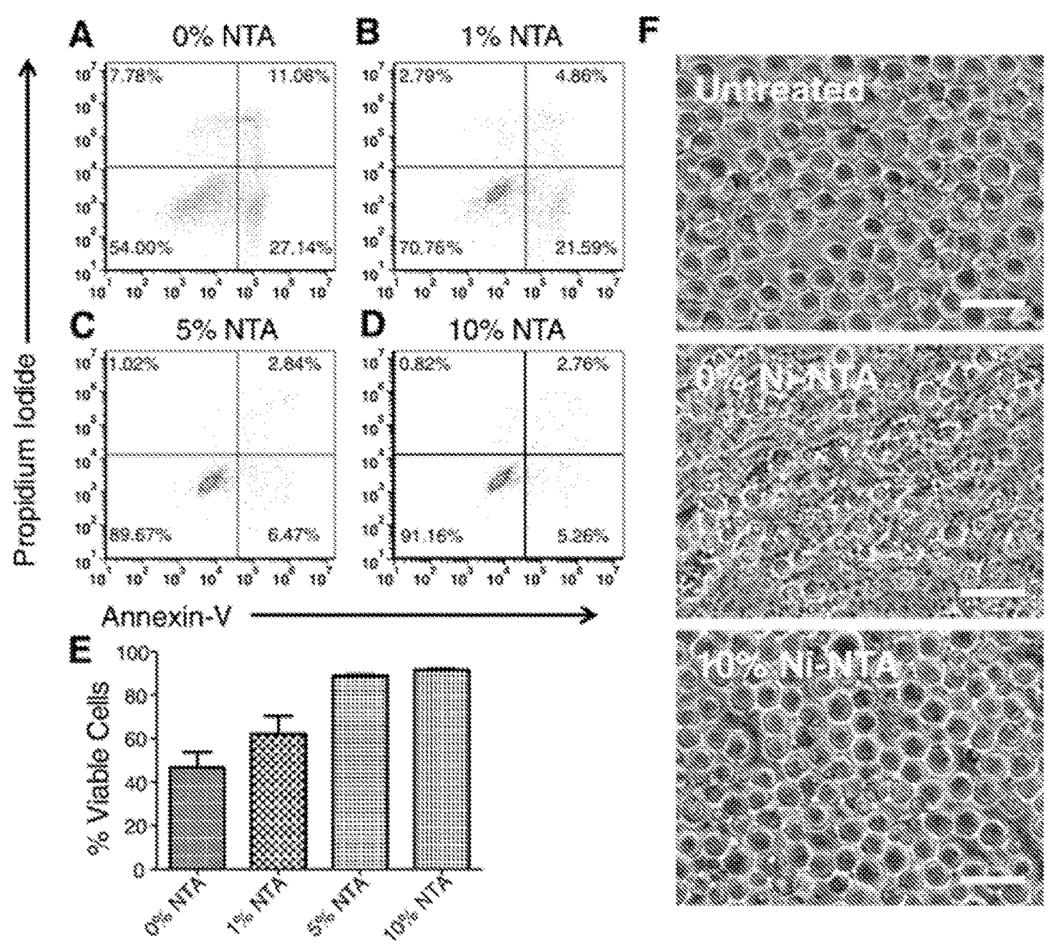
FIG. 7. Incorporation of Ni-NTA conjugated lipids on liposomes maximizes protein conjugation to the liposome surface. To determine how much Ni-NTA conjugated lipid is required to bind TRAIL and ES to the liposome surface, COLO 205 cells were incubated with supernatant left after liposome preparation and assayed for cell viability. Increased cell death is indicative of more unbound TRAIL protein in solution. (A-D) Annexin-V apoptosis assay of COLO 205 cell viability after incubation with supernatant of liposomes conjugated to 0% (A), 1% (B), 5% (C), and 10% Ni-NTA (D) post-ultracentrifugation, with varying amounts of Ni-NTA conjugated to the liposome surface. Cells were classified into four categories based on dye uptake: viable cells (negative for Annexin-V and propidium iodide (PI)), early apoptotic cells (positive for Annexin-V only), late apoptotic cells (positive for Annexin-V and PI) and necrotic cells (positive for PI only). (E) COLO 205 cell viability after treatment with unbound TRAIL and ES in liposome supernatant. n=3 for all samples. Bars represent the mean±SD in each treatment group. (F) Representative micrographs of untreated COLO 205 cells (top) and those treated with the supernatant of liposomes conjugated to 0% (middle) and 10% Ni-NTA (bottom). 10% Ni-NTA conjugated lipid on the liposome leads to nearly complete incorporation onto the liposome surface. Scale bar=50 μm.
Figure 8:
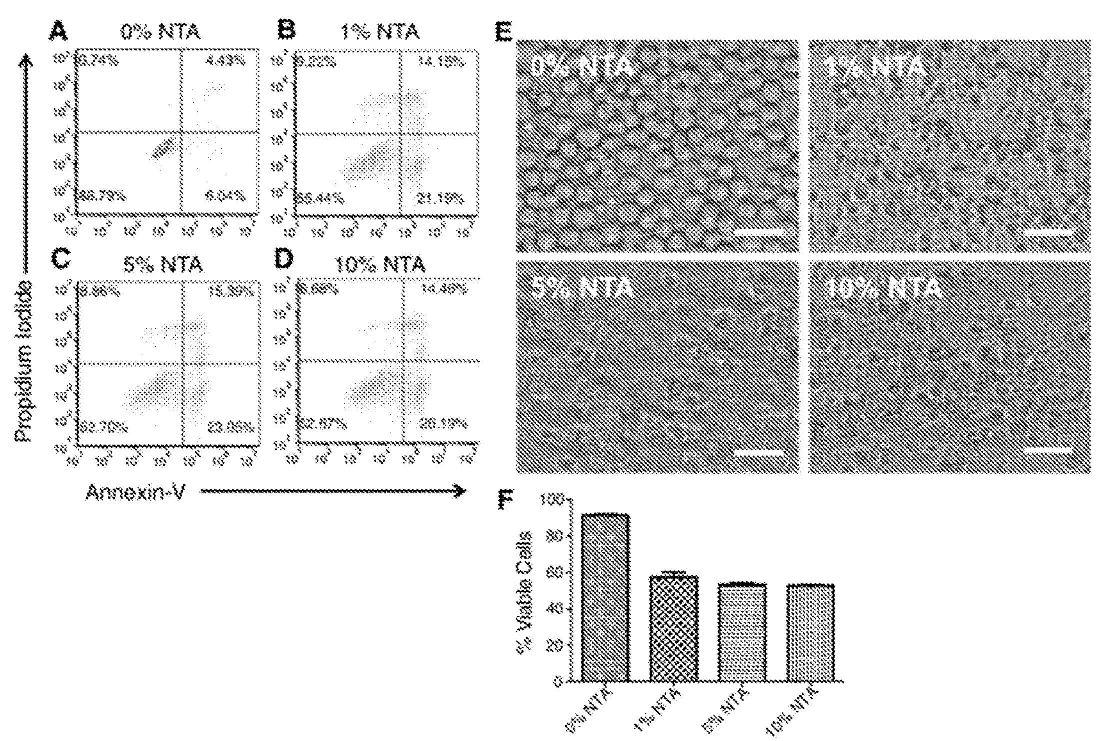
FIG. 8. ES/TRAIL liposomes are somewhat effective in targeting and killing COLO 205 cells under static conditions. (A-D) Annexin-V apoptosis plots of COLO 205 cells treated with ES/TRAIL liposomes consisting of 0% (A), 1% (B), 5% (C), and 10% Ni-NTA (D) for 24 h. (E) Representative micrographs showing COLO 205 cells after 24 h incubation with liposomes. Scale bar=50 μm. (F) COLO 205 cell viability following incubation with liposomes with varying amounts of Ni-NTA on the liposome surface. n=3 for all samples. Bars represent the mean±SEM in each treatment group.

ES/TRAIL liposomes adhesively interact and induce apoptotic cancer cell death under shear flow. Many types of circulating tumor cells (CTC), and cancer cell lines derived from colon, breast, prostate, and pancreas are known to display glycosylated ligands that allow them to adhesively interact with E-selectin (ES) under physiological shear flow. This has been proposed to explain why some cancers home to tissue specific capillary beds such as the bone marrow and liver. To target and kill cancer cells of this form, we used nanoscale liposomes conjugated with a mixture of recombinant human E-selectin (ES) protein and tumor necrosis factor (TNF)-related apoptosis inducing ligand were developed (TRAIL; FIG. 1A, FIG. 7 and Table 1). ES/TRAIL liposomes consisting of a 10% weight ratio of DOGS-Ni-NTA, utilized to conjugate ES and TRAIL to the liposome surface, were found to be most effective at inducing apoptotic cell death in a colorectal adenocarcinoma (COLO 205) cell line under static conditions (FIG. 8), as determined using an Annexin-V apoptosis assay.

TABLE 1

Weight ratios of liposome formulations (with increasing amounts of Ni-NTA0conjugated lipid, the corresponding amount of egg PC lipid was decreased.

| DOGS NTA-Ni | Egg PC (wt %) | Egg SM (wt %) | Chol.Bdp-Chol (wt %) |
|---|---|---|---|
| 0% NTA | 60 | 30 | 10 |
| 1% NTA | 59 | 30 | 10 |
| 5% NTA | 55 | 30 | 10 |
| 10% NTA | 50 | 30 | 10 |

In the post-capillary venules where selectin-mediated adhesion and cell extravasation into tissues typically occur, moderate shear rates can initiate flowing cell interactions with the endothelial cell wall. To recreate these physical forces in vitro, a cone-and-plate shear assay was developed to probe the interactions of cancer cells and ES/TRAIL liposomes under venular shear rates. After exposure to shear flow (shear rate: 188 $s^{-1}$) for 2 h, COLO 205 cells exposed to ES liposomes displayed their normal morphology, while substantial membrane blebbing was observed in those exposed to ES/TRAIL liposomes, characteristic of cells undergoing apoptosis (FIG. 1B). Annexin-V assay revealed that exposure to shear flow for 2 h induced minimal COLO 205 cell apoptosis in untreated controls (FIG. 1C), in addition to treatment with liposomes in the absence of conjugated protein (FIG. 1D) or conjugated solely with ES (FIG. 1E) or TRAIL (FIG. 1F). However, a combination of ES/TRAIL conjugated to the liposome surface induced a significant decrease in COLO 205 viability following exposure to shear flow (FIG. 1G, H).

Figure 9:
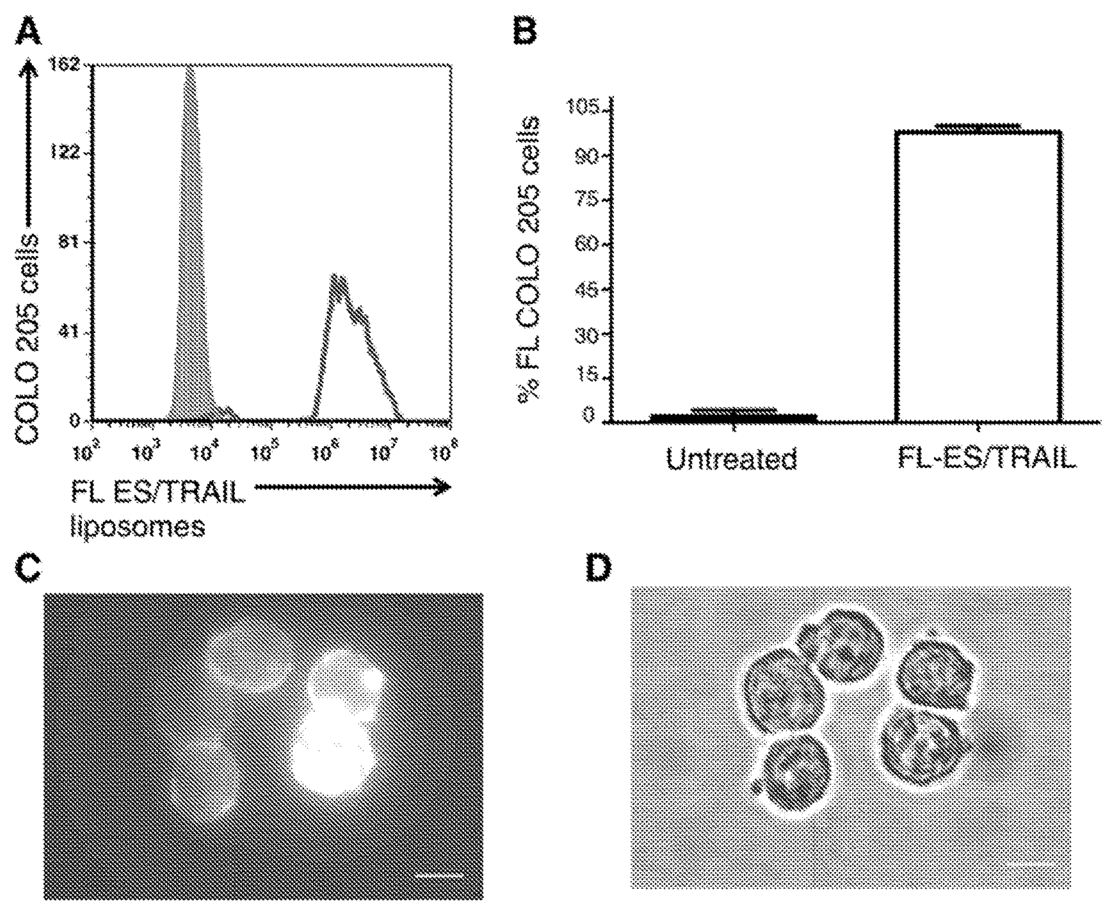
FIG. 9. ES/TRAIL liposomes adhesively interact with cancer cells. (A) Flow cytometry plots of cancer cells positive for fluorescently tagged ES/TRAIL liposomes (green). Grey population represents fluorescence of COLO 205 cells in the absence of fluorescent ES/TRAIL liposomes. (B) Percent of COLO 205 cells adhered to liposomes following shear flow at a shear rate of 188 $s^{-1}$. n=3 for all samples. Bars represent the mean±SEM in each treatment group. (C,D) Representative fluorescent (left) and bright-field overlay (right) micrographs of COLO 205 cells adhered to fluorescently tagged liposomes following shear flow. Scale bar=20 μm.

To investigate the adhesive characteristics of ES/TRAIL liposomes to cancer cells under flow, COLO 205 cells were exposed to ES/TRAIL liposomes consisting of fluorescent cholesterol and exposed to shear flow as in previous in vitro shear assays. Flow cytometry revealed that >99.9% of the COLO 205 cell population was adhered to ES/TRAIL liposomes after exposure to shear flow (FIG. 9A,B). Fluorescent micrographs and brightfield overlay images clearly displayed ES/TRAIL liposomes adhered to the surface of COLO 205 cells (Fig. S3C,D). These data suggest that the presence of the ES adhesion receptor enhances the effect of TRAIL by promoting tighter contacts with the cancer cell membrane.

Figure 2:
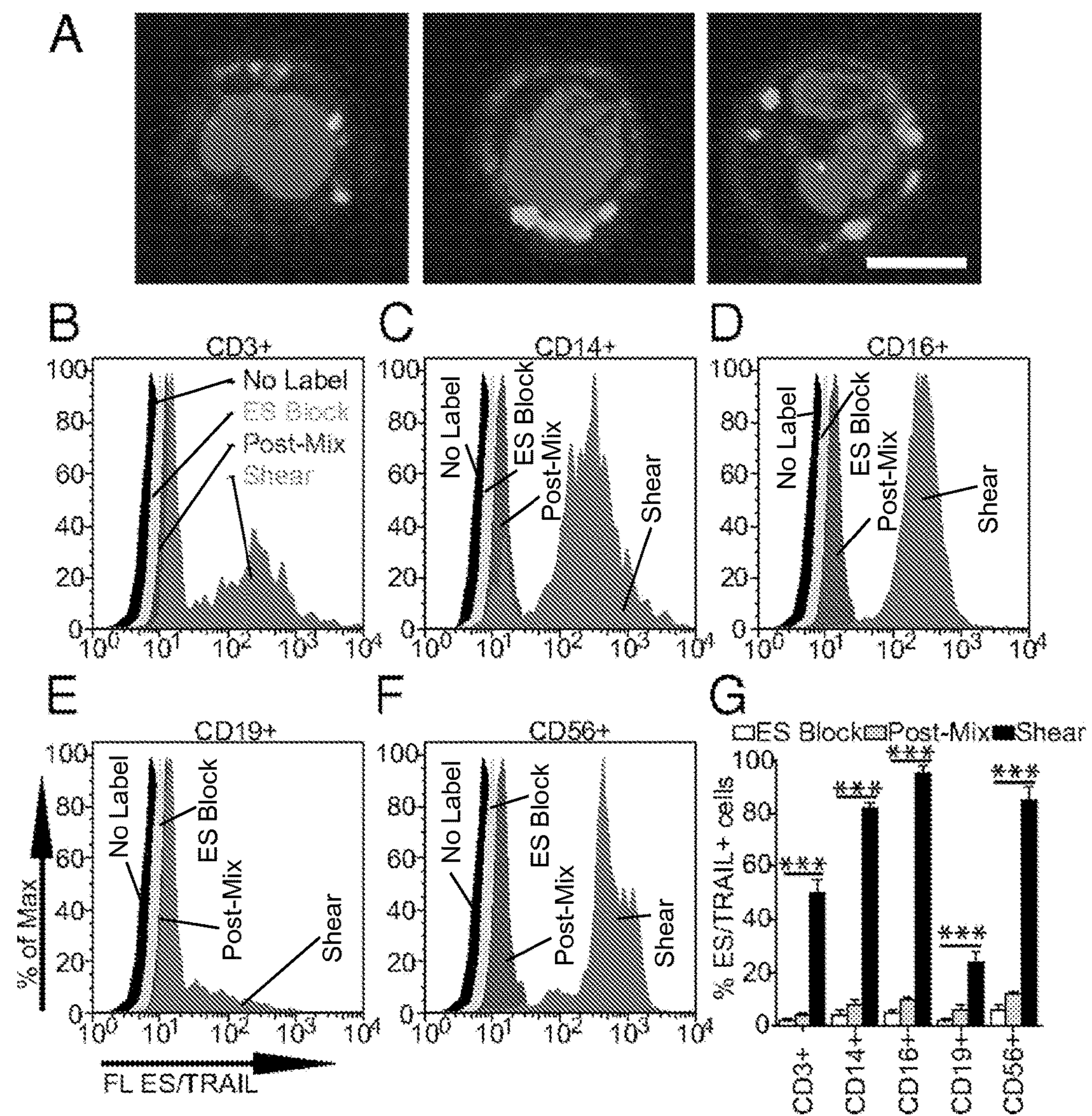
FIG. 2. ES/TRAIL liposomes adhere to multiple leukocyte subpopulations after exposure to shear flow in whole blood. (A) Confocal images of ES/TRAIL liposomes (green) bound to human leukocytes (blue=cell nuclei) after exposure to shear flow in whole blood in a cone-and-plate viscometer at 188 $s^{-1}$ for 30 min Leukocytes have nuclear morphology characteristic of monocytes (left), lymphocytes (middle), and neutrophils (right). Scale bar=5 μm. (B-G) To assess which leukocyte subpopulations ES/TRAIL liposomes adhesively interact with, fluorescent ES/TRAIL liposomes were added to human blood and exposed to shear flow in a cone-and-plate viscometer at a shear rate of 188 $s^{-1}$ for 30 min Leukocytes were isolated from blood using a Polymorphs density gradient, and labeled with CD3, CD14, CD16, CD19, and CD56, which is typically expressed on T-lymphocytes, monocytes, neutrophils, B-lymphocytes, and natural killer cells, respectively. Expression of fluorescent ES/TRAIL (FL ES/TRAIL) liposomes on the surface of leukocytes that are CD3+(B), CD14+(C), CD16+(D), CD19+(E), and CD56+(F), determined using flow cytometry. Expression of CD3, CD14, CD16, CD19, and CD56 on the leukocyte surface was determined using isotype controls. No label: unsheared cells that were not treated with fluorescent ES/TRAIL liposomes. ES block: cells treated with fluorescent ES/TRAIL liposomes that were pretreated with an ES functional blocking antibody. Post-mix: cells labeled with fluorescent ES/TRAIL liposomes immediately after mixing liposomes in whole blood. (G) Percent of CD3+, CD14+, CD16+, CD19+, and CD56+ leukocytes adhered to ES/TRAIL liposomes. n=3 for all samples. Bars represent the mean±SD in each treatment group. ***P<0.0001 (one-way ANOVA with Tukey post test).

ES/TRAIL liposomes functionalize leukocytes in whole blood under shear flow in vitro. In addition to CTCs, circulating leukocytes also possess ligands for E-selectin, which are necessary in the inflammatory response and lymphocyte homing to lymphatic tissues. To assess the potential to functionalize leukocytes with ES/TRAIL to target and kill CTC, we treated whole human blood with fluorescent ES/TRAIL liposomes under shear flow in a cone-and-plate viscometer. Upon exposure to shear (shear rate: 188 $s^{-1}$), ES/TRAIL liposomes readily bind to leukocytes via selectin ligands on the leukocyte surface (FIG. 2A).

To quantify leukocyte subpopulations that adhere to ES/TRAIL liposomes under flow, leukocytes were separated from whole blood and analyzed for both leukocyte marker expression and adherent ES/TRAIL liposomes using flow cytometry. Functionalized leukocytes were labeled with CD3, CD14, CD16, CD19, and CD56 antibodies, as such markers are commonly expressed on most T-lymphocytes, monocytes, neutrophils, B-lymphocytes, and natural killer (NK) cells, respectively. Minimal adhesion of ES/TRAIL liposomes to leukocytes in blood was observed in the presence of a functional blocking ES antibody (FIG. 2B-G). Minimal ES/TRAIL liposome adhesion was also observed immediately after treatment with whole blood. However, after exposure to shear flow, flow cytometry analysis revealed that leukocyte subpopulations positive for CD3 (FIG. 2B), CD14 (FIG. 2C), CD16 (FIG. 2D), CD19 (FIG. 2E), and CD56 (FIG. 2F) adhered to ES/TRAIL liposomes to varying degrees (FIG. 2G). Adhesion was also observed on populations of lymphocytes, which suggests that some cytotoxic patrolling of the lymphatic system may also occur in vivo. Leukocyte subpopulations can vary in their E-selectin ligand expression and thus could explain the variations in the number of bound ES/TRAIL liposomes.

Figure 10:
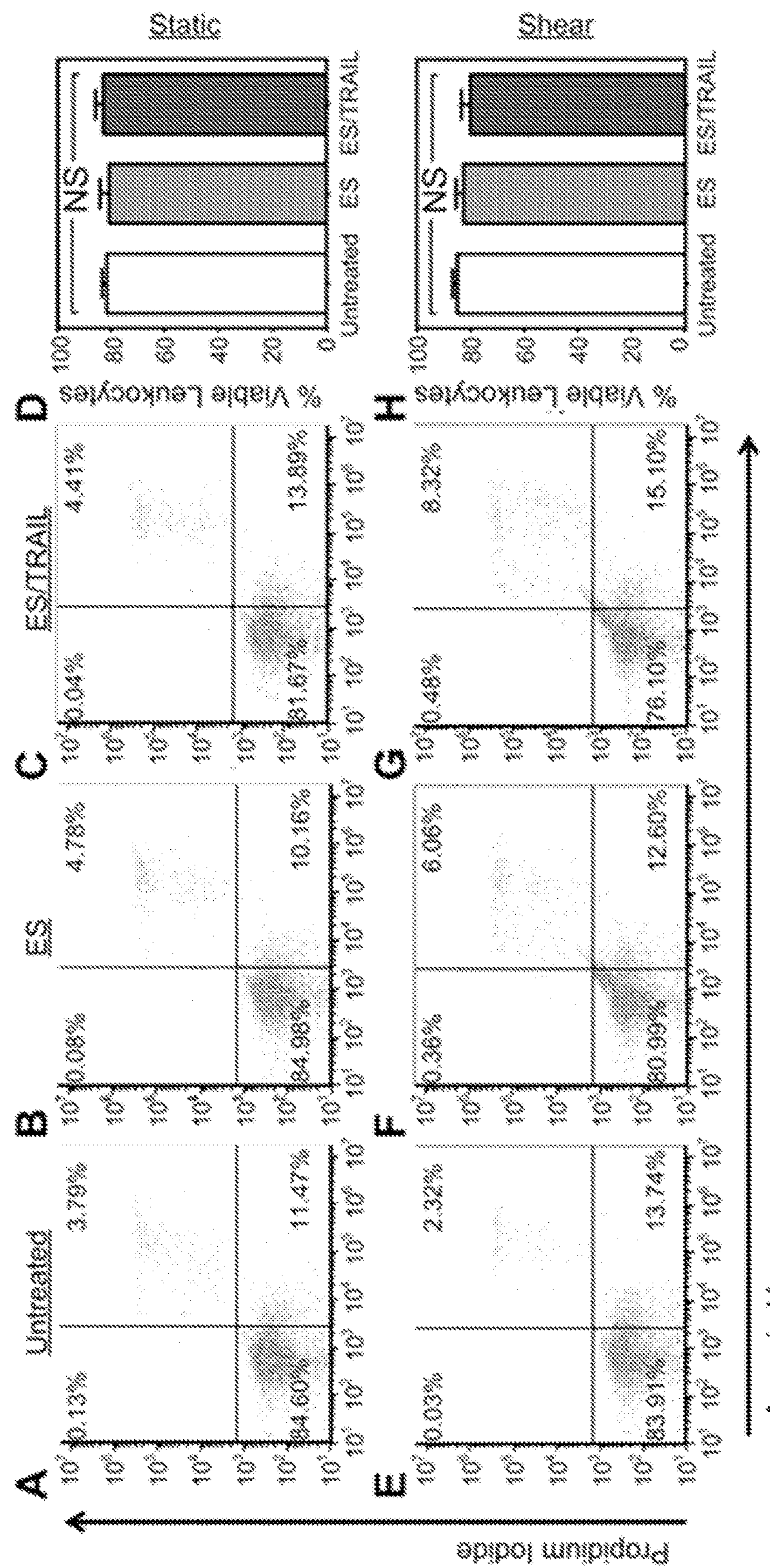
FIG. 10. Leukocyte functionalization with ES/TRAIL does not induce significant leukocyte death. (A-C) Representative propidium iodide/Annexin-V flow cytometry plots of untreated mononuclear cells (A) and those treated with ES (B) and ES/TRAIL (C) liposomes under static conditions for 24 h. (D) Viability of mononuclear cells following incubation with liposomes for 24 h. n=3 for all samples. Bars represent the mean±SEM in each treatment group. NS: not significant (one-way ANOVA with Tukey post test). (E-G) Representative propidium iodide/Annexin-V flow cytometry plots of untreated mononuclear cells (E) and those treated with ES (F) and ES/TRAIL (G) liposomes under shear flow (shear rate: 188 $s^{-1}$) for 2 h. (H) Viability of MNCs treated with liposomes under shear flow for 2 h. n=3 for all samples. Bars represent the mean±SD in each treatment group. NS: not significant (one-way ANOVA with Tukey post test).

ES/TRAIL functionalization does not induce significant leukocyte or endothelial cell death. To assess the effects of ES/TRAIL functionalization on leukocyte viability, mononuclear leukocytes isolated from human blood were treated with ES/TRAIL liposomes under both static and shear flow conditions. Annexin-V assays revealed no significant differences in leukocyte viability when leukocytes were incubated with ES (FIG. 10B) or ES/TRAIL (FIG. 10C) liposomes under static conditions for 24 h, compared to untreated leukocyte controls (FIG. 10A,D). Upon functionalization with liposomes under shear flow for 2 h (shear rate: 188 $s^{-1}$), no significant decreases were found in ES (FIG. 10F) or ES/TRAIL (FIG. 10G) functionalized leukocytes, compared to untreated leukocyte controls (FIG. 10E, H). These data suggest that ES/TRAIL liposomes can functionalize leukocytes under flow to target and kill cancer cells, while exerting negligible cytotoxic effects on leukocytes.

Figure 11:
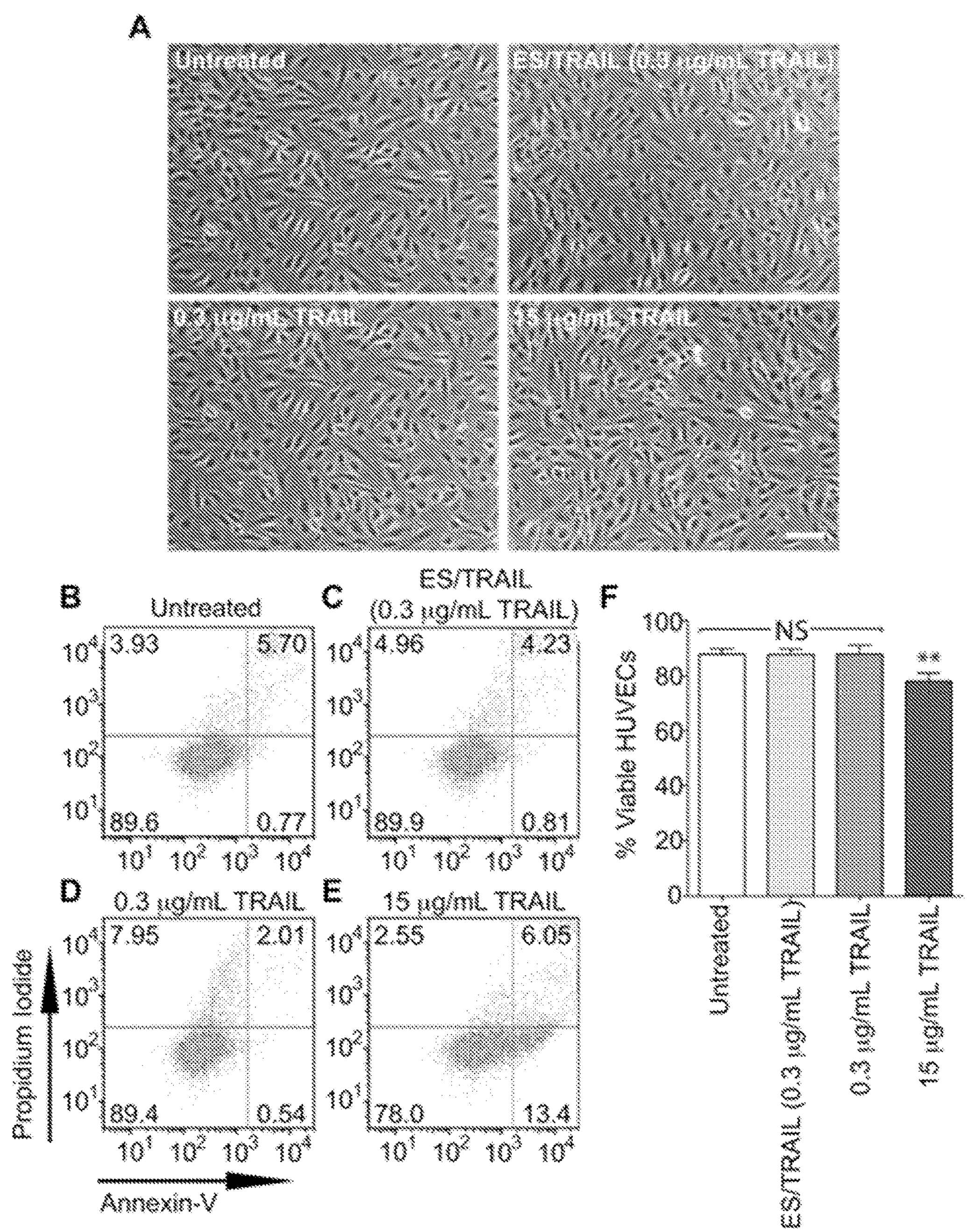
FIG. 11. Leukocyte functionalization with ES/TRAIL does not induce significant endothelial cell death. (A) Representative images of HUVECs immobilized on coverslips immediately after treatment in human blood, with various drug treatments, under shear flow (shear rate: 188 $s^{-1}$) for 4 h at 37° C. Scale bar=100 μm. (B-D) Representative propidium iodide/Annexin-V flow cytometry plots of untreated HUVECs (B) and those treated with ES/TRAIL liposomes (C; TRAIL concentration: 0.3 μg/mL) or soluble TRAIL (D; TRAIL concentration: 0.3 μg/mL) in human blood under shear flow for 4 h at 37° C. (E) As a positive control, HUVECs were treated with a high dosage of TRAIL (15 μg/mL) in human blood under shear flow for 4 h at 37° C. HUVECs were classified into four categories based on dye uptake: viable cells (negative for Annexin-V and propidium iodide (PI)), early apoptotic cells (positive for Annexin-V only), late apoptotic cells (positive for Annexin-V and PI) and necrotic cells (positive for PI only). (F) Percent viability of HUVECs after various drug treatments in human blood under shear flow for 4 h at 37° C. n=3 for all samples. Bars represent the mean±SD in each treatment group. **P<0.001. NS: not significant (one-way ANOVA with Tukey post test).

To assess the effects of ES/TRAIL functionalization on endothelial cell viability, human umbilical vein endothelial cells (HUVEC) were treated with ES/TRAIL liposomes in human blood under shear flow conditions in vitro. Treatment with ES/TRAIL liposomes or an equivalent concentration of soluble TRAIL in human blood under shear flow for 4 h induced no significant differences in HUVEC viability, compared to untreated HUVEC exposed to shear in human blood (FIG. 11). These data suggest that ES/TRAIL-functionalized leukocytes exert negligible toxic effects on human endothelial cells under blood flow conditions.

Figure 3:
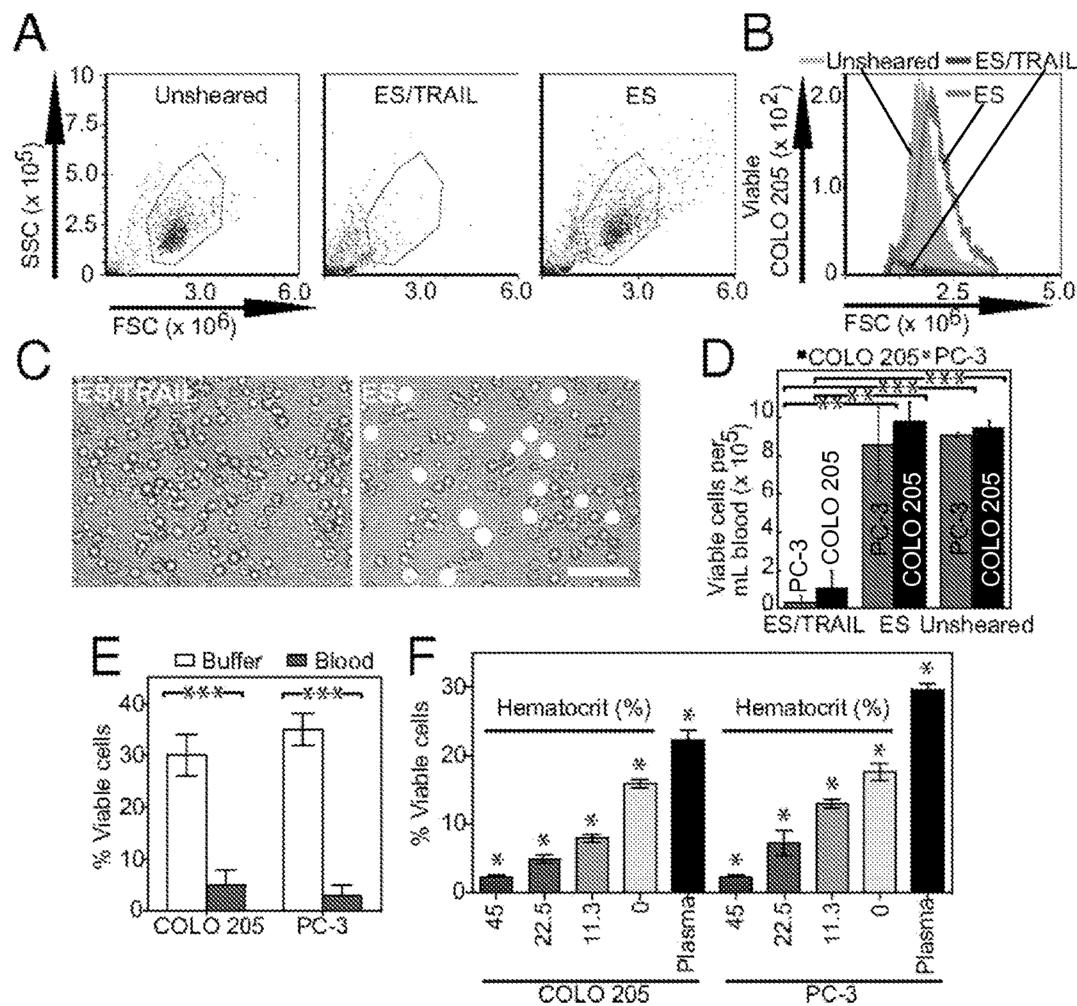
FIG. 3. ES/TRAIL liposome therapeutic effects are enhanced in human blood under flow in vitro. (A) Flow cytometry of COLO 205 cancer cells after treatment with ES/TRAIL or ES liposomes in blood under shear flow in a cone-and-plate viscometer at 188 $s^{-1}$ for 2 h. Unsheared: viable untreated cancer cell control. (B) Representative flow cytometry histogram showing the number of viable cancer cells collected. (C) Representative micrographs of COLO 205 cells (white) in blood when treated with ES/TRAIL (left) and ES only (right) liposomes in blood under shear flow. Scale bar=50 μm. (D) Number of viable COLO 205 and PC-3 cells per volume of blood after treatment with ES/TRAIL or ES liposomes in blood under shear flow. n=3 for all samples. Bars represent the mean±SD in each treatment group. P<0.001, *P<0.0001 (unpaired t-test). (E) Comparison of fraction of COLO 205 and PC-3 cells that remained viable after treatment with ES/TRAIL liposomes in buffer versus blood. n=3 for all samples. Bars represent the mean±SD in each treatment group. ***P<0.0001 (unpaired t-test). (F) Fraction of COLO 205 and PC-3 cells that remained viable after treatment with ES/TRAIL liposomes in blood with varying percentages of normal hematocrit. Hematocrit was varied while other blood components remained constant, based on a normal hematocrit of 45%. Plasma indicates removal of all blood cells. n=3 for all samples. Bars represent the mean±SD in each treatment group. *P<0.05 (one-way ANOVA with Tukey post test).

Apoptotic effects of ES/TRAIL therapy are enhanced in human blood under flow. Clinically, CTCs are sparsely distributed in the complex milieu of whole blood, at concentrations as low as 1-100 cells/mL. To examine whether ES/TRAIL liposomes would effectively target cancer cells in the presence of blood cells and serum under flow conditions, we fluorescently labeled colorectal COLO 205 and prostate PC-3 cancer cell lines and spiked them into human peripheral blood. Surprisingly, under identical shear flow conditions ES/TRAIL therapy was even more effective at killing cancer cells in the presence of human blood (FIG. 3A-D), compared to shearing COLO 205 or PC-3 cells alone in buffer (FIG. 3E), with <5% of the fluorescent, viable cancer cell populations remaining after ES/TRAIL treatment (FIG. 3E). These results suggest that ES/TRAIL therapy is effective at targeting circulating cancer cells derived from multiple organs in human blood.

To evaluate the impact of blood cells on the efficacy of ES/TRAIL treatment, fluorescent COLO 205 and PC-3 cells were spiked in human blood of varying hematocrit percentages. All additional blood cell components were maintained, while the volume of removed erythrocytes was replaced with plasma from the same blood donor. Interestingly, the apoptotic effects were hematocrit-dependent, as higher hematocrit significantly decreased the number of viable COLO 205 and PC-3 cells after ES/TRAIL treatment (FIG. 3F). The enhanced apoptotic effect suggests that blood cell collisions under flow can promote the apoptotic effects of ES/TRAIL liposomes.

Figure 4:
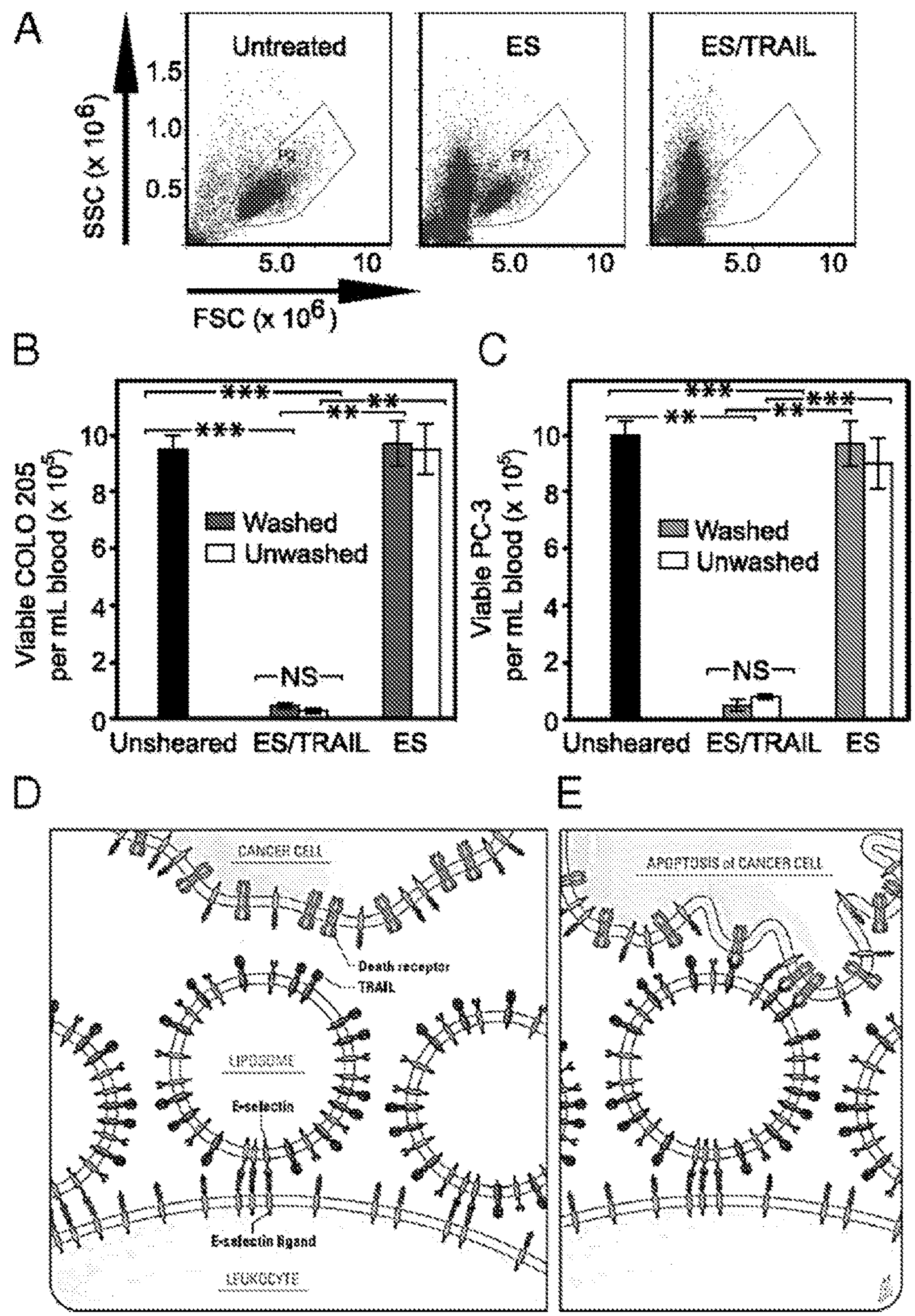
FIG. 4. ES/TRAIL liposomes functionalize leukocytes under shear flow in vitro to target and kill cancer cells. (A) Flow cytometry plots of COLO 205 cells in untreated samples (left) and when treated in human blood with ES (middle) or ES/TRAIL (right) functionalized leukocytes (but no unbound liposomes) under shear flow. (B,C) Number of viable COLO 205 (B) and PC-3 (C) cells per volume of blood after treatment with leukocytes functionalized with ES/TRAIL or ES liposomes, but with no unbound liposomes, in human blood (Washed), or after treatment with ES or ES/TRAIL liposomes in blood (Unwashed). n=3 for all samples. Bars represent the mean±SD in each treatment group. P<0.001, *P<0.0001 (unpaired t-test). (D,E) Schematic of the two-step mechanism involving decoration of leukocytes with liposomes (D), which then contact circulating cancer cells and activate the death receptor (E).
Figure 12:
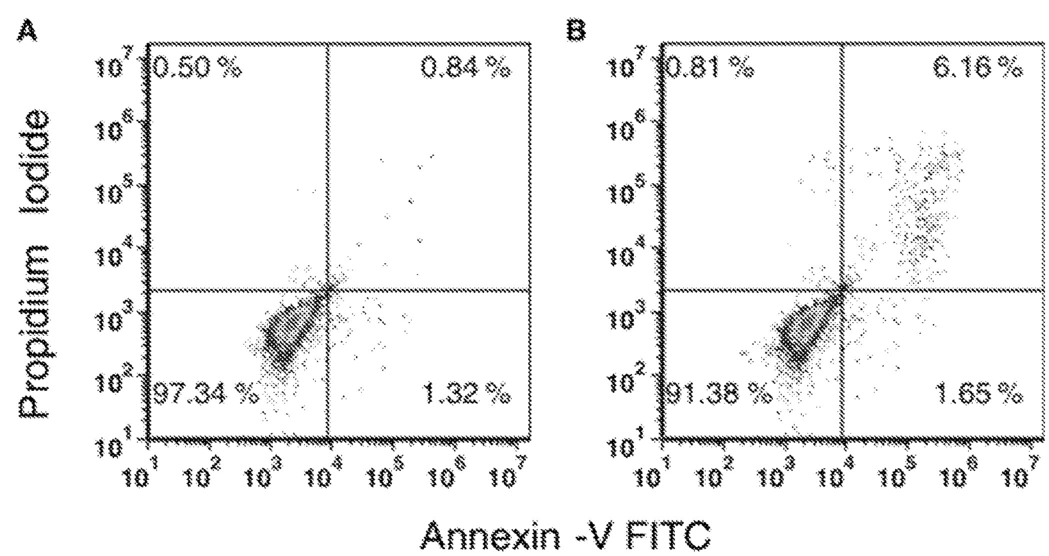
FIG. 12. Low toxicity of blood plasma after treatment with ES/TRAIL liposomes. (A) Viability of COLO 205 cells after treatment with plasma from normal healthy blood for 24 h. (B) Viability of COLO 205 cells after treatment with plasma extracted from blood that had been sheared with ES/TRAIL liposomes for 30 min Cells were incubated with plasma and any remaining unbound ES/TRAIL liposomes and/or liposome fragments in the plasma for 24 h, and analyzed for cell viability.
Figure 13:
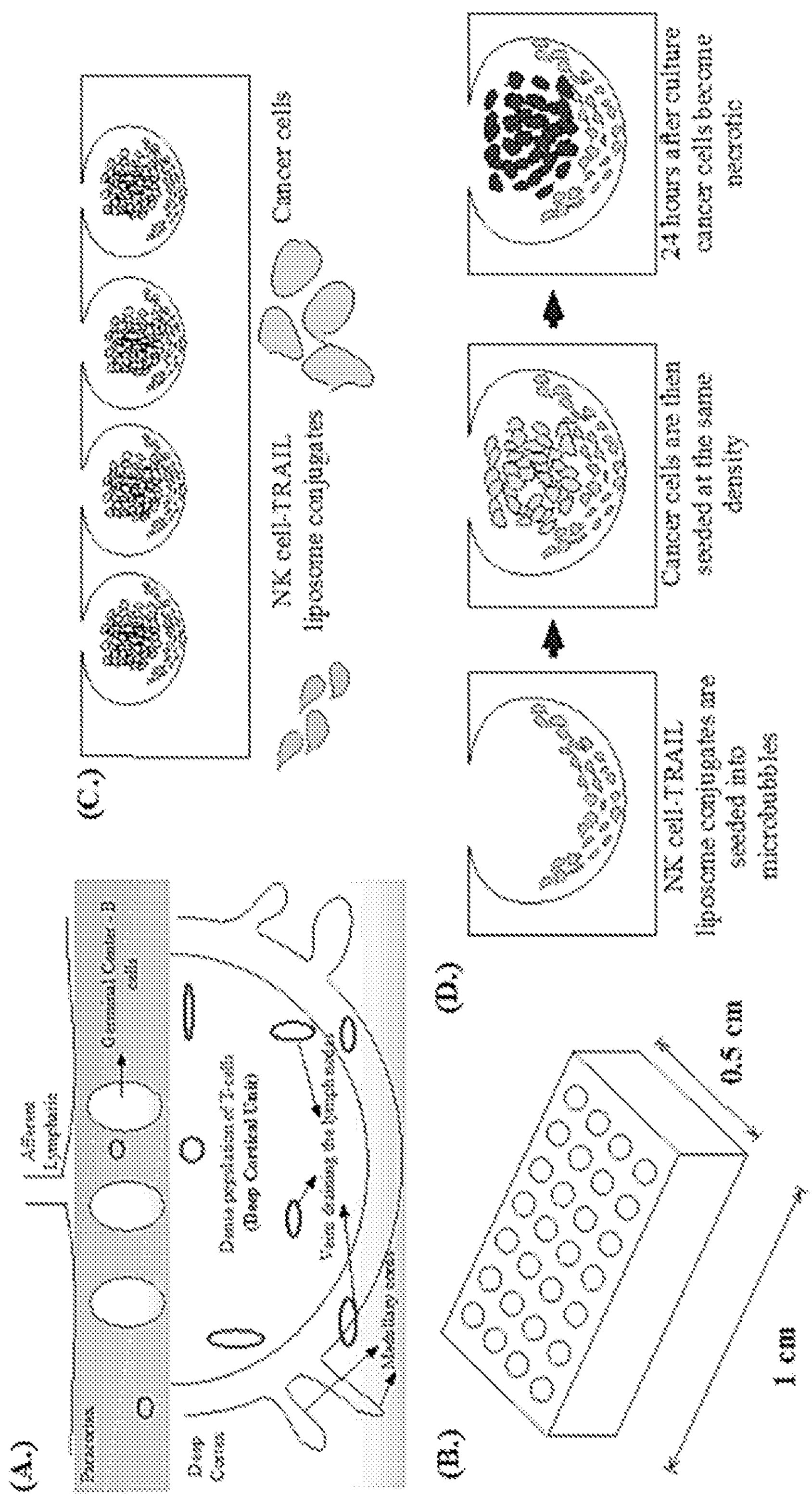
FIG. 13: Schematic diagram of (A.) Deep cortical unit of a lymph node (B.) Array of MB on a single chip (C.) Cancer cells co-cultured with NK cell-TRAIL liposome conjugates in MB (D.) Single MB showing our approach.

To assess the mechanism by which leukocytes act as a pervading carrier surface for functional TRAIL, blood was pretreated with ES/TRAIL liposomes under shear flow, with blood cells subsequently separated from unbound ES/TRAIL via centrifugation and replaced with fresh blood plasma. ES/TRAIL therapeutic effects under shear flow remained nearly identical, as COLO 205 and PC-3 cells spiked into a suspension of blood with washed, pretreated blood cells were killed at roughly the same rate as unwashed blood (FIG. 4A-C). Thus, upon addition of the ES/TRAIL liposomes to cancer cell-spiked blood, liposomes attach to the surface of leukocytes, and are available for inducing apoptosis in cancer cells that they come into contact with (FIG. 4D,E). As an indicator of unbound ES/TRAIL liposomes and/or liposome fragments remaining in human blood after shearing pretreatment, the toxicity of supernatant collected from pretreated blood was tested in COLO 205 culture. An Annexin-V assay showed minimal COLO 205 cell death after treatment with a supernatant of human plasma and unbound ES/TRAIL, compared to cells treated with plasma supernatant alone (FIG. 12). These data suggest that ES/TRAIL liposomes readily bind to the surface of leukocytes, with minimal unbound liposomes remaining, to target and kill cancer cells under flow.

Figure 5:
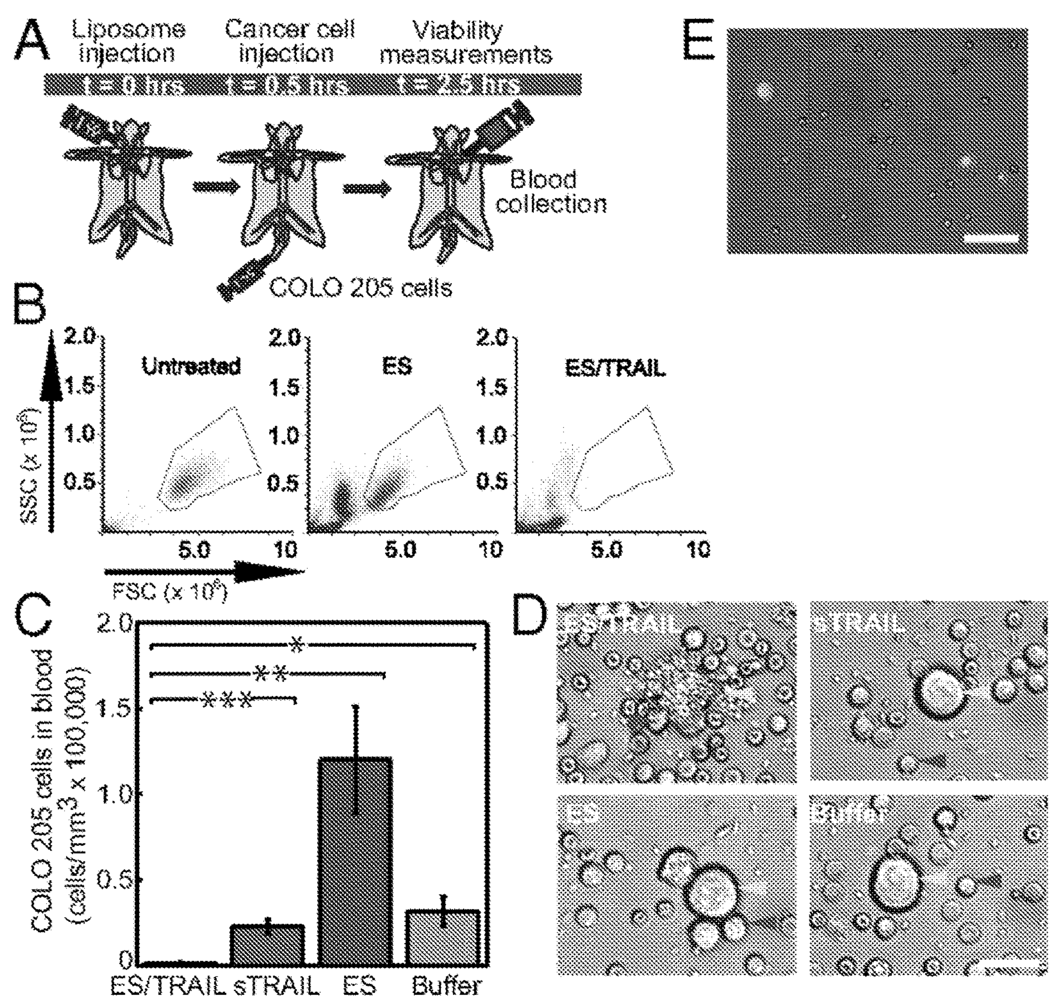
FIG. 5. ES/TRAIL functionalized leukocytes target and kill cancer cells in the circulation of mice in vivo. (A) Schematic of in vivo mouse experiment. (B) Flow cytometry of untreated COLO 205 cancer cells (left) and those recovered from cardiac puncture from mice treated with ES (middle) and ES/TRAIL liposomes (right). (C) Number of viable cancer cells recovered per volume of mouse blood for mice treated with ES/TRAIL liposomes, soluble TRAIL (sTRAIL), ES liposomes, and buffer injections. n=3 for all samples. Bars represent the mean±SD in each treatment group. *P<0.01, P<0.001, *P<0.0001 (one-way ANOVA with Tukey post test). (D) Representative micrographs of COLO 205 cells removed from circulation in mice treated with ES/TRAIL liposomes (top left), sTRAIL (top right), ES liposomes (bottom left), and buffer (bottom right) injections. Scale bar=20 μm. (E) Leukocytes functionalized with fluorescent ES/TRAIL liposomes (green, seen as bright in black & white) upon removal from mouse circulation 2.5 h after injection. Scale bar=50 μm.

ES/TRAIL functionalized leukocytes reduce number of viable cancer cells in mouse circulation in vivo. To assess the cytotoxic effects in vivo, ES/TRAIL liposomes were also tested for their ability to kill cancer cells flowing in the peripheral circulation of mice. Two million fluorescently labeled COLO 205 cells were injected into the tail vein of immunocompetent C57BL/6J mice, 30 min after injection of 120 μL of either ES/TRAIL liposomes, ES liposomes, or soluble TRAIL (FIG. 5A). Tail vein injection was utilized to model leukocyte/CTC interactions in mouse circulation, as this technique has been an accepted and widely used model of lung metastasis. For these studies, the use of recombinant human E-selectin was continued because of its ability to bind both human COLO 205 cancer cells and mouse neutrophils, which were previously shown to have cross reactivity and roll on E-selectin. Mice were sacrificed 2.5 h after the initial injection, and cancer cells were recovered from the circulation via cardiac puncture. Cancer cells were placed back into culture for 2-3 h before the number of viable cells were quantified.

Using flow cytometry, we measured ~130,000 cancer cells/mL blood for mice injected with control ES liposomes, compared to <2,000 cancer cells/mL blood surviving from ES/TRAIL treated mice (FIG. 5B,C). Mice injected with buffer or soluble TRAIL had intermediate numbers of cells (FIG. 5C) compared to ES and ES/TRAIL-treated samples, likely indicating that ES functionalized liposomes help to retain cancer cells in the circulation by blocking selectin-mediated interaction of the COLO 205 cells with the endothelium. Brightfield micrographs of COLO 205 cells exposed to buffer and soluble TRAIL showed characteristic cancer cell morphology (FIG. 5D). Micrographs of COLO 205 cells exposed to ES revealed adherent leukocytes on the COLO 205 cell surface without significant morphological change, while, whereas the cancer cells from ES/TRAIL-treated mice showed notable membrane blebbing of COLO 205 cells in the proximity of leukocytes (FIG. 5D). To assess the adhesion of ES/TRAIL liposomes to leukocytes in mouse circulation, mice were injected with ES/TRAIL liposomes tagged with fluorescent cholesterol, and were allowed to circulate for 2.5 h. Brightfield overlay micrographs showed that leukocytes recovered from the mouse circulation were functionalized with ES/TRAIL liposomes (FIG. 5E), suggesting that ES/TRAIL remains functionalized to leukocytes, which can exert cytotoxic effects onto cancer cells in mouse circulation.

Figure 6:
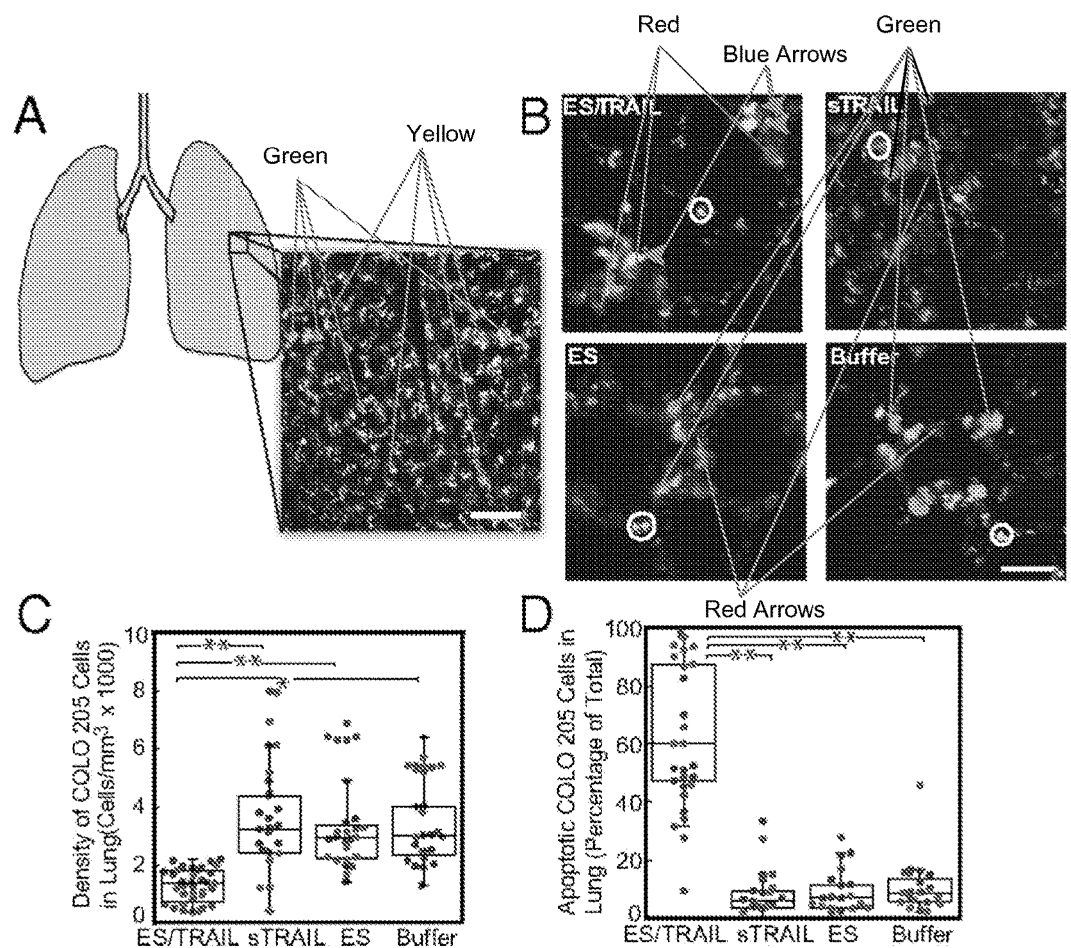
FIG. 6. Decreased number and increased apoptosis in COLO 205 cells lodged in mouse lung after treatment with ES/TRAIL liposomes. (A) Schematic of mouse lung and example two-photon excited fluorescence (2PEF) image stack from mouse lung where Hoechst-labeled COLO 205 cells (green) are arrested in lung tissue (visible by autofluorescence, yellow). Scale bar=80 μm. (B) 2PEF images of Hoescht-labeled COLO 205 cells (green) with Alexa Flour 568 labeled Annexin V apoptosis probe (red) for each experimental group. Red arrows point to apoptotic COLO 205 cells (red and green colocalized), blue arrows indicate non-apoptotic COLO 205 cells (green only). White circles indicate regions of autofluorescence from lung tissue. Scale bar=30 μm. (C) Density of COLO 205 cells lodged in the lung for each experimental group. (D) Percentage of lodged COLO 205 cells positive for Annexin-V probe for each experimental group. Individual data points represent data from one image stack, with points shown in the same color representing image stacks from the same animal. Superimposed box plots bound the 25th to 75th percentage of all data points and the whiskers extend 1.5 times the interquartile range beyond the boxes. The horizontal lines within the boxplot represent the median. n=3 animals for each experimental group. *P<0.01, **P<0.0001 (one-way ANOVA with Tukey post test).

ES/TRAIL treatment reduces number and increases apoptosis of remaining circulating COLO 205 cells lodged in vivo in mouse lung. Previous studies have shown that more than 90% of tumor cells that enter the vasculature via tail vein injection lodge into lung vasculature within the first two hours. To assess the viability of the remaining circulating cancer cells lodged within mice, fluorescent COLO 205 cells lodged within the lungs of mice were identified using two-photon excited fluorescence microscopy (FIG. 6A,B) Immediately following euthanasia, the lungs were resected, and two-photon images were acquired in three regions of the lung that were identical for each animal, to obtain an accurate estimate of cell counts (FIG. 6A). Roughly twice as many cells were found in the ES, sTRAIL, and buffer treated animals as the ES/TRAIL treated animals (FIG. 6C), suggesting many COLO 205 cells had already died and degenerated. The cancer cell density found in lung suggests about 1.4 million cancer cells were lodged in the lung for buffer treated animals (assuming a lung volume of ~0.4 mL), representing the bulk of the two million COLO 205 cells injected.

We then evaluated the apoptotic effects of ES/TRAIL liposomes on cancer cells that have already lodged into the lungs of mice. After the injections of liposomes and COLO 205 at previously used time points (FIG. 5A), we injected a solution of Annexin-V tagged with a fluorescent Alexa 594 dye to assess for phosphatidylserine flipping on the COLO 205 cell membrane, characteristic of apoptosis. Mouse lungs were imaged using two-photon microscopy to determine whether Hoescht-labeled COLO 205 cells were also positive for Annexin-V labeling. In addition to the decreased density of cancer cells lodged in mouse lung (FIG. 6C) we also found a dramatic increase in apoptosis of the cancer cells (FIG. 6B,D) in the ES/TRAIL liposome treated mice as compared with other groups. Soluble TRAIL protein injected into mice following the same protocol displayed minimal cytotoxic activity comparable to control, as expected due to its short circulation half-life. Mice injected with ES/TRAIL liposomes survived for over two weeks with no loss in body weight (n=3). These data suggests that ES/TRAIL treatment serves to decrease the number of remaining circulating COLO 205 cells lodged in mouse lung, while increasing the fraction of them that are apoptotic.

Natural killer cells, activated by interleukin-2 or other factors, are induced to present TRAIL protein on their surface. These cells participate in immunosurveillance against micrometastases in the body, and comprise 10-20% of peripheral blood mononuclear cells. While the liposome-coated leukocytes described here are not specifically programmed to actively invade tissues and seek out solid tumors, they do have frequent opportunities for incidental contact with CTCs in the bloodstream and there may be some degree of homing of normally-functioning leukocytes to solid tumors. We find that TRAIL is most potent when it is tethered to the surface of leukocytes in shear flow—rather than freely soluble or on untethered liposomes in the absence of blood. Tethering nanoscale liposomes to the surface of peripheral blood leukocytes is also beneficial for increasing liposome circulation time, by avoiding renal clearance mechanisms.

While not intending to be bound by any particular theory, it is believed that the much higher cytotoxic activity in shear flow of leukocytes coated with ES/TRAIL liposomes have, compared to isolated ES/TRAIL liposomes or soluble TRAIL protein may be due to compressive force between surfaces. Two spherical particles colliding in linear shear flow will experience a compressive force between them which scales as $F_c \sim \mu * G * a * b$, where μ is the fluid viscosity, G is the shear rate, and a and b are the radii of the smaller and larger sphere, respectively. Thus, a 10 μm diameter leukocyte colliding with a cancer cell may experience 100 times the compressive force of a 100 nm liposome colliding with a cancer cell. Compressive forces could flatten down any cell surface glycocalyx composed of biologically inert macromolecules, thus allowing TRAIL to come within a reactive distance to the cancer cell death receptors and form bonds.

Recombinant human TRAIL/Apo2L, also known as PRO1762 developed by Amgen/Genentech, has been the subject of numerous Phase 1, la, 2, and 3 clinical trials over the past decade, with minimal adverse effects reported. There are many intracellular proteins, such the inhibitors of apoptosis protein (IAPs) family members that also confer TRAIL resistance to normal cells. Additionally, the dosages of TRAIL used in this current study ranged from 0.06-0.08 mg/kg, two orders of magnitude lower than the clinical dosages of 1-30 mg/kg used in human clinical trials. While different types of cancer cells show different levels of sensitivity to TRAIL-induced apoptosis, it has been well documented that there is a wide range of agents known to sensitize cancer cells to TRAIL-mediated apoptosis, including conventional chemotherapeutics (camptothecin, cisplatin, doxorubicin, 5-fluorouracil, irinotecan, paclitaxel, gemcitabine), proteasome inhibitors, Bcl-2 inhibitors, IAP antagonists, HDAC inhibitors, CD20 antibodies, irradiation, synthetic triterpenolds, Sorafenib, aspirin, and natural products such as curcumin and piperlongumine.

Example 2

This example describes the use of nanoparticles functionalized with an cancer-specific apoptosis ligand TRAIL and an antibody to CD57. These nanoparticles were used in a model for lymph node micrometastases.

Materials and Methods

Microfabrication of silicon wafers and microbubble formation. A lithography mask was designed with using AutoCAD LT 2008 (Autodesk, Inc., USA). The mask included three different types arrays of rectangular trenches with 60 μm, 100 μm and 200 μm circular openings. Depth of the trenches was 150 μm. Silicon wafers were produced from this mask (MEMS and Nanotechnology Exchange, Virginia USA) using the Bosch deep reactive ion etching (DRIE) process. The hydrophobic coating produced during the Bosch process was left intact. The DRIE silicon wafers were used to produce microbubble in PDMS. Dow Corning's Sylgard® 184 silicone elastomer kit in a 10:1 base to curing agent ratio (w/w) was manually mixed in a 50 mL tube for 2 min and poured onto silicon wafers. The mixture was allowed to spread out on the wafer for 30 min at room temperature and cured at 100° C. for 2 hr. The PDMS was then peeled off from the wafers and the arrays were cut in small chips to be used in cell culture experiments. The experiments described in this work were all performed on microbubbles formed from the 100 μm circular openings on the wafer.

Cell lines and culture conditions. Three lymph node seeking metastatic cell lines from different types of cancers were used in this study. LNCaP (prostate cancer), COLO 205 (colorectal cancer) and MDA-MB-231 (breast cancer) were purchased from American Type Culture Collection (ATCC) and maintained in culture at 37° C. with 5% $CO_2$ in humidified incubator. LNCaP and COLO205 cells were cultured in RPMI-1640 (Cellgro, 10-040-CV) supplemented with 10% fetal bovine serum (FBS) (Atlanta Biologicals, 511050H), and 1% penicillin/streptomycin (PS) (Gibco®, 15140-122). MDA-MB-231 cells were cultured in high glucose DMEM (Gibco®, 11965-092) supplemented with 10% FBS and 1% PS. HNK-1, a hybridoma cell line (ATCC® TIB-200™) was cultured in RPMI-1640 (ATCC® 30-2001™) supplemented with 0.02 mM 2-mercaptoethanol (Gibco®, 21985-023) and 20% ultra low IgG FBS (Gibco®, 16250-078). The hybridoma line secretes anti-CD57 (IgM isotype), a monoclonal antibody against human natural killer cells.

Preparation of TRAIL and anti-CD57 functionalized liposomes. Hydro Soy PC L-α-phosphatidylcholine (HSPC), cholesterol, 1,2-distearoyl-sn-glycero-3-phosphoethanolamine-N-[methoxy (polyethylene glycol)-2000] (DSPE-mPEG2000) and 1,2 distearoyl-sn-glycero-3-phosphoethanolamine-N-[maleimide (polyethylene glycol)-2000] (DSPE-Mal-mPEG2000) were purchased from Avanti Polar Lipids (Alabaster, Ala., USA). Liposomes were composed of HSPC:cholesterol:DSPE-mPEG200:DSPE-Mal-mPEG2000 at a molar ratio of 2:1:0.08:0.02. Lipids were mixed to produce a total of 10 mM lipid in 1 mL and kept in a glass vial covered with parafilm inside a vacuum glass chamber over night to remove residual organic solvent. The lipid cake was then hydrated in 1 mL of buffer composed of 20 mM 4-(2-hydroxyethyl)-1-piperazineethanesulfonic acid (HEPES) and 150 mM sodium chloride in phosphate buffered saline (PBS) at pH 7.5. The hydrated lipids formed multi-lamellar vesicles and they were then disrupted by 10-15 freeze (2 min)/thaw (3 min) cycle before extrusion. The lipid suspension was then forced through a polycarbonate filter with successively smaller pore size (400 nm, 200 nm and 100 nm) mounted on a holder in a heating block (Avanti® mini-extruder). The temperature was maintained at 60° C. above the phase transition temperature of the lipids.

Anti-CD57 was isolated from hybridoma supernatant using a protein-L agarose column (Thermoscientific, 20510) following a protocol supplied by the manufacturer for gravity-flow based isolation of proteins. Recombinant human TRAIL (Peprotech 310-04) and anti-CD57 were thiolated using 1 mM Traut's reagent (Thermoscientific, 26101) added in 6-fold molar excess to the proteins in solution. Excess Traut's reagent was removed using a desalting column (Thermoscientific, 89889) by spinning the reaction mixture three times for 2 min at 1000×g. Thiolated proteins were then functionalized on the surface of liposomes overnight at 4° C. via maleimide-thiol chemistry by adding an appropriate amount of protein to set the concentration of maleimide in liposomes at 6-fold molar excess to the concentration of thiol groups in proteins. The protein-functionalized liposome was stored at 4° C. for up to a week and was prepared fresh whenever required. Successful functionalization of proteins to liposomes was determined by measuring the average particle size by dynamic light scattering using a Malvern Zetasizer nano ZS (Malvern Instruments Ltd., UK).

To produce fluorescent liposomes used in this study, cholesterol in the lipid composition was replaced with TopFluor cholesterol (Avanti polar lipids, 810225). The same protocol was used to make fluorescent liposomes by minimizing the exposure to light.

Conjugation of liposomes to natural killer cells. Natural killer cells were isolated from whole blood of healthy volunteers using the RosetteSep™ human NK cell enrichment cocktail (Stemcell technologies, 15065) following the protocol supplied by the manufacturer. NK cells were maintained in culture using Myelocult™ (Stemcell technologies, H5100) supplemented with 1 mM hydrocortisone and 100 U/mL of human recombinant interleukin-2 (IL-2) (Millipore, IL002).

For conjugating CD57-expressing NK cells to anti-CD57 and TRAIL functionalized liposomes, NK cells were pelleted and resuspended in 200 μL of 2% bovine serum albumin (BSA). They were then incubated with a specific volume of protein-functionalized liposomes at 4° C. for 1 hr. The volume of liposomes to be added to $1\times10^6$ NK cells was determined by incubating $1\times10^6$ NK cells with 5, 10, 25 and 50 μl of fluorescent liposomes. The NK cells were then washed twice with PBS to remove any unbound liposomes by centrifuging them at 1000 rpm for 10 min. The fluorescent intensity histograms from flow cytometric analysis (BD Accuri™ C6 flow cytometer) were used to determine the optimum volume of liposomes to be added to $1\times10^6$NK cells. Successful conjugation of liposomes to NK cells was verified using flow cytometry and fluorescent microscopy with appropriate filters on an Olympus IX81 microscope. NK cells conjugated to TRAIL-functionalized liposomes are referred to herein as "super NK cells". To ensure that there were no deleterious effects of conjugating TRAIL-functionalized liposomes to NK cells, conjugated cells were cultured in vitro for 24 hr and stained for live cell marker Calcein-AM (Molecular Probes®, C3100MP).

Characterization of cell lines for death receptor expression. Cancer cells were analysed for the expression of death receptors (DR4 and DR5) using flow cytometry (Guava Easycyte™ flow cytometer). LNCaP, COLO 205 and MDA- MB-231 cells grown to confluence in 6-well plates were washed with PBS and cells were harvested using enzyme-free cell dissociation buffer (Gibco®, 13151-014). Approximately $0.5\times10^6$ cells were resuspended in 100 μL 2% BSA. Cells were then incubated with 10 μL of PE-conjugated monoclonal antibody against DR4 (R&D Systems, FAB347P) and DR5 (R&D Systems, FAB6311PS) and 10 μl of corresponding isotype control (R&D Systems, IC0041P) at 4° C. for 45 min. Following incubation, unreacted antibodies were removed by washing with PBS twice by centrifugation at 1000 rpm for 5 min. Cells were resuspended in 400-600 μL of 1% BSA for flow cytometric analysis.

Cell culture experiments in MB arrays. Super NK cells were co-cultured with cancer cells in MB arrays at 37° C. for 24 hr. For co-culturing super NK cells and cancer cells in MB arrays, we followed the protocol described in detail previously[48]. Briefly, small chips (1 cm×0.5 cm) containing arrays of MB were rinsed in 70% ethanol and distilled water and dried with nitrogen gas. The backside of the chips was rendered hydrophilic by etching them in a plasma chamber with atmospheric air for 10 min to keep the chips submerged in cell culture media. The chips were then blocked and subjected to negative pressure in a vacuum chamber to remove the air trapped inside the microbubbles during the curing process. NK cells were conjugated to TRAIL-functionalized liposomes as described in Section 2.4 and about $0.1\times10^6$ super NK cells were resuspended in 200 μL cell culture media composed of RPMI-1640 supplemented with 10% FBS and 1% PS. Approximately 100 μL of the cell stock solution was applied to top of the chip and incubated for 30 min at room temperature (25° C.) under sterile conditions. After incubation, the cell solution was removed and the chip was rinsed twice to remove any cells that may have deposited on the surface outside the spherical cavities. After seeding super NK cells, about $0.1\times10^6$ cancer cells (LNCaP, COLO205 and MDA-MB-231) in 200 μL of cell culture media was applied to the top of the chip and incubated for 10-15 min. The chips were rinsed twice and then placed inside a single well of a 24-well plate filled with 1 mL of cell culture media. The 24-well plate containing the MB chips was placed inside a humidified cell culture chamber maintained at 37° C. with 5% $CO_2$.

The following control conditions were used in the cell culture experiments. Before seeding MB arrays with cancer cells, MB arrays were incubated with liposome buffer, naked liposomes (liposome without TRAIL), TRAIL-functionalized liposomes, unmodified NK cells.

In situ detection of apoptotic cancer cells. To determine the therapeutic efficacy of the proposed approach, cells cultured in MB arrays were stained in situ using an apoptosis detection kit (Trevigen®, 4840-01-K). The kit is based on Annexin V-FITC to label early apoptotic cells and propidium iodide (PI) to label late apoptotic/necrotic cells. Incubation reagent was prepared using a protocol provided by the manufacturer. The reagent was further diluted 1:10 times in 2% BSA. The MB chips were removed from 24-well plates and 100 μL of diluted reagent was applied on top of the MB chips. The chips were incubated for 30 min at room temperature in the dark. After incubation, the chips were washed gently 5-10 times by immersing them in a well containing PBS. The chips were then imaged using an Olympus IX81 microscope with appropriate filters for FITC and PI. Images were taken at 12 hr and 24 hr after culture to label apoptotic cancer cells.

Digital images from fluorescence microscopy were processed using ImageJ after normalizing for background intensity (NIH, USA). A region of interest was defined around each microbubble for analysis of Annexin V-FITC and PI staining. Areas were analysed for the mean intensity and the values are reported as bar graphs for a quantitative measure of apoptotic cancer cells in MB arrays. The mean pixel intensity between different treatment groups was compared for statistical significance using unpaired student t-test.

Confocal microscopy. NK cells were labelled with CellTracker green (Molecular Probes®, C7025) and LNCaP cells were labelled with CellTracker red (Molecular Probes®, C34552) and seeded on MB arrays following the protocol mentioned in Section 2.6. The chips were then transferred into a glass bottomed 24-well plate and imaged using a Zeiss 710 laser scanning confocal microscope.

Results

Figure 19:
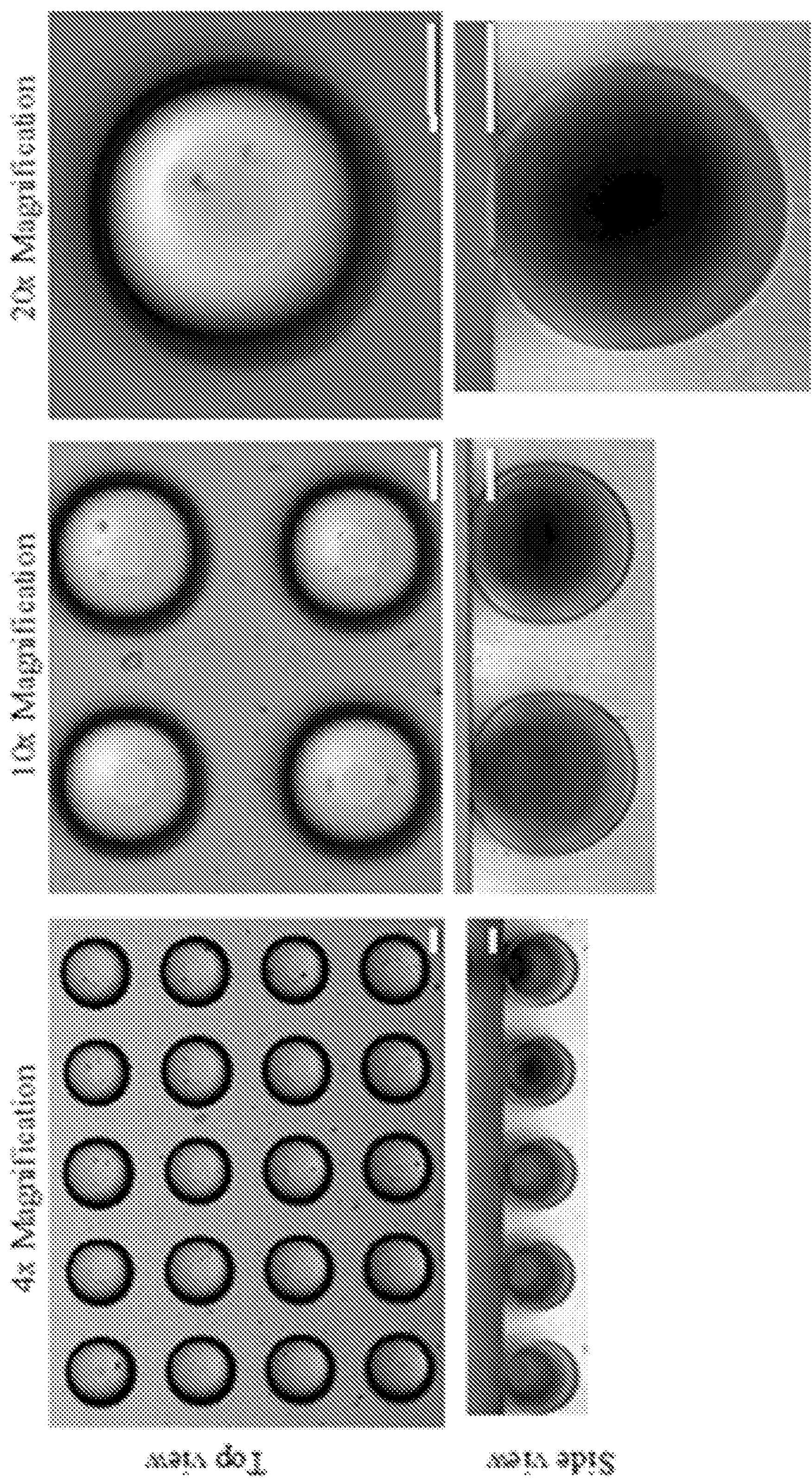
FIG. 19. Top view and side view of microbubble (MB) arrays formed from 100 μm circular openings at different magnifications. Scale bar=100 μm.

Microbubbles geometry closely recapitulates the anatomy of deep cortical unit of a lymph node. In this work we were interested in developing a unique application of MB arrays as a model for mimicking lymph node micrometastases. Their semi-rounded geometry with a single circular opening on the top closely resembles the semi-rounded anatomy of a deep cortical unit of a lymph node centered on the top of an afferent lymphatic. PDMS is a commonly used polymer for cell culture applications. Apart from mimicking the deep cortical unit of a lymph node in terms of anatomy, PDMS provides a realistic mechanical loading to cells. The elastic modulus of PDMS is 50-200 kPa, which is very close to the modulus of several soft tissues including lymph nodes. The top view and side view of MB formed from 100 μm circular openings are shown in FIG. 19.

Figure 14:
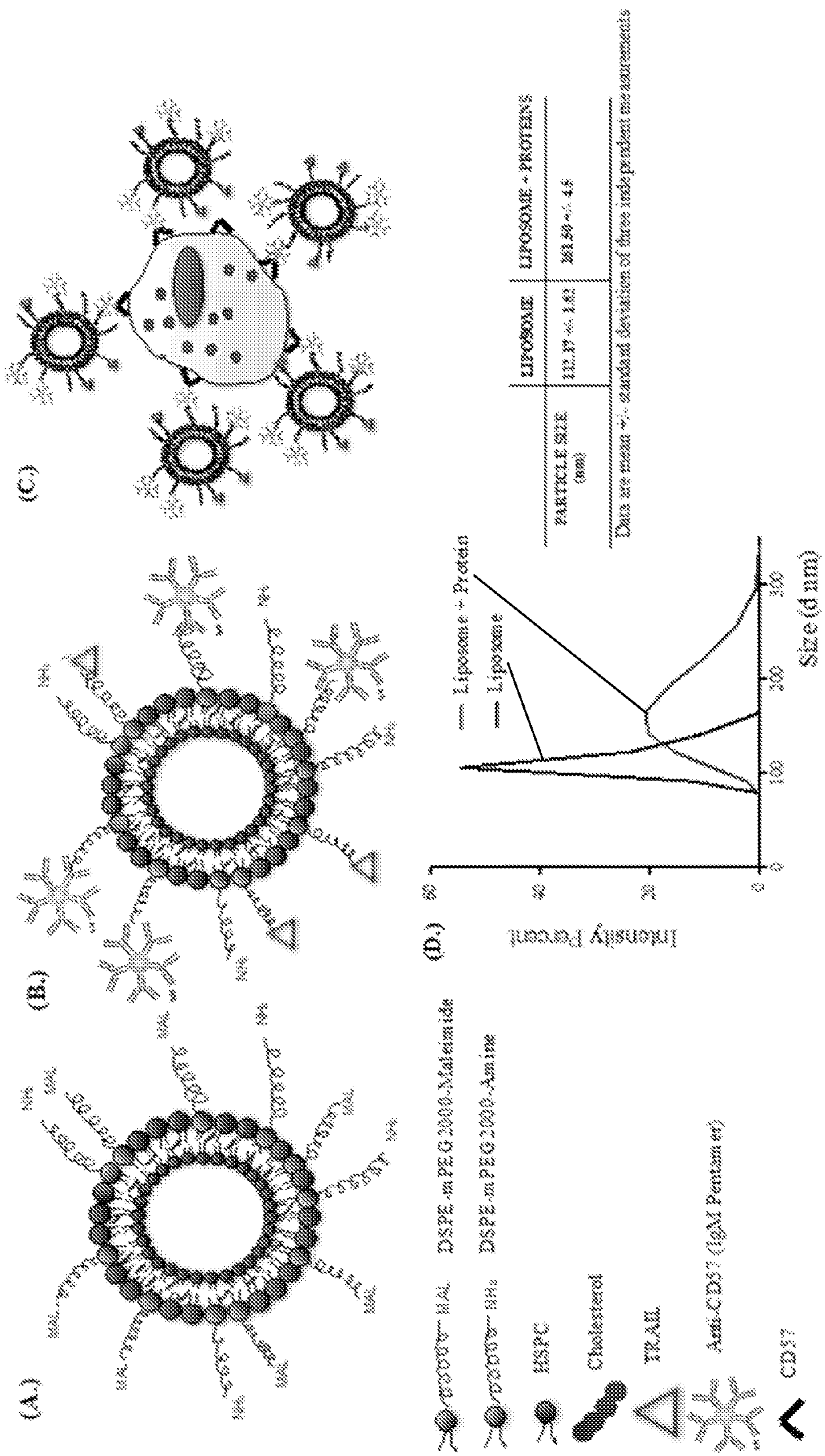
FIG. 14. Schematics of a (A.) naked liposome (B.) TRAIL and anti-CD57 functionalized liposome (C.) NK cell-liposome conjugate (Super NK cell) (D.) Size distribution of naked liposomes and protein-functionalized liposomes from Malvern zetasizer instrument. Table indicates the average size of particles in each group.
Figure 20:
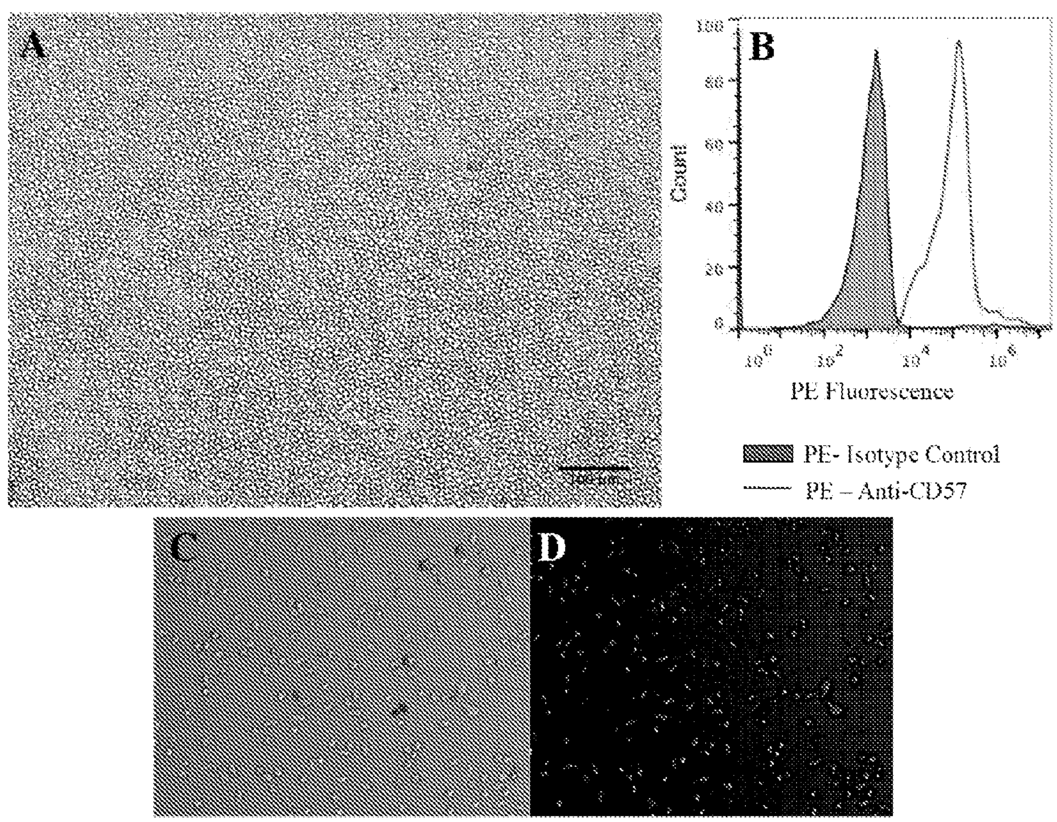
FIG. 20. (A). NK cells in culture 24 hours after isolation. (B) Expression of CD57 by NK cells. (C) Bright field image of NK cells conjugated to TRAIL functionalized liposomes. (D) Fluorescent field image of NK cells stained with Calcein-AM (Live cell marker) 24 hours after conjugation indicates that TRAIL functionalized liposomes did not have any detrimental effects on NK cells.

Characterization of TRAIL and anti-CD57 functionalized liposome. Successful functionalization of TRAIL and anti-CD57 on the liposome surface is mediated by maleimide-thiol conjugation as indicated in FIGS. 14A and 14B. NK cells isolated from whole blood were maintained in culture (FIG. 20A) and flow cytometry histograms indicated that NK cells were positive for CD57 expression (FIG. 20B). CD57 is a marker for terminal differentiation in T-cells and it is expressed by a distinctly mature subpopulation of human NK cells. The size distribution of naked liposomes and protein-functionalized liposomes was analysed using a zetasizer. The average size of naked liposomes was 112.17±1.62 nm and TRAIL and anti-CD57 functionalized liposomes were roughly 45-55 nm larger than naked liposome (FIG. 14D). The increase in size of liposomes after protein incubation indicated that TRAIL and anti-CD57 have been functionalized on the surface of liposomes.

Figure 15:
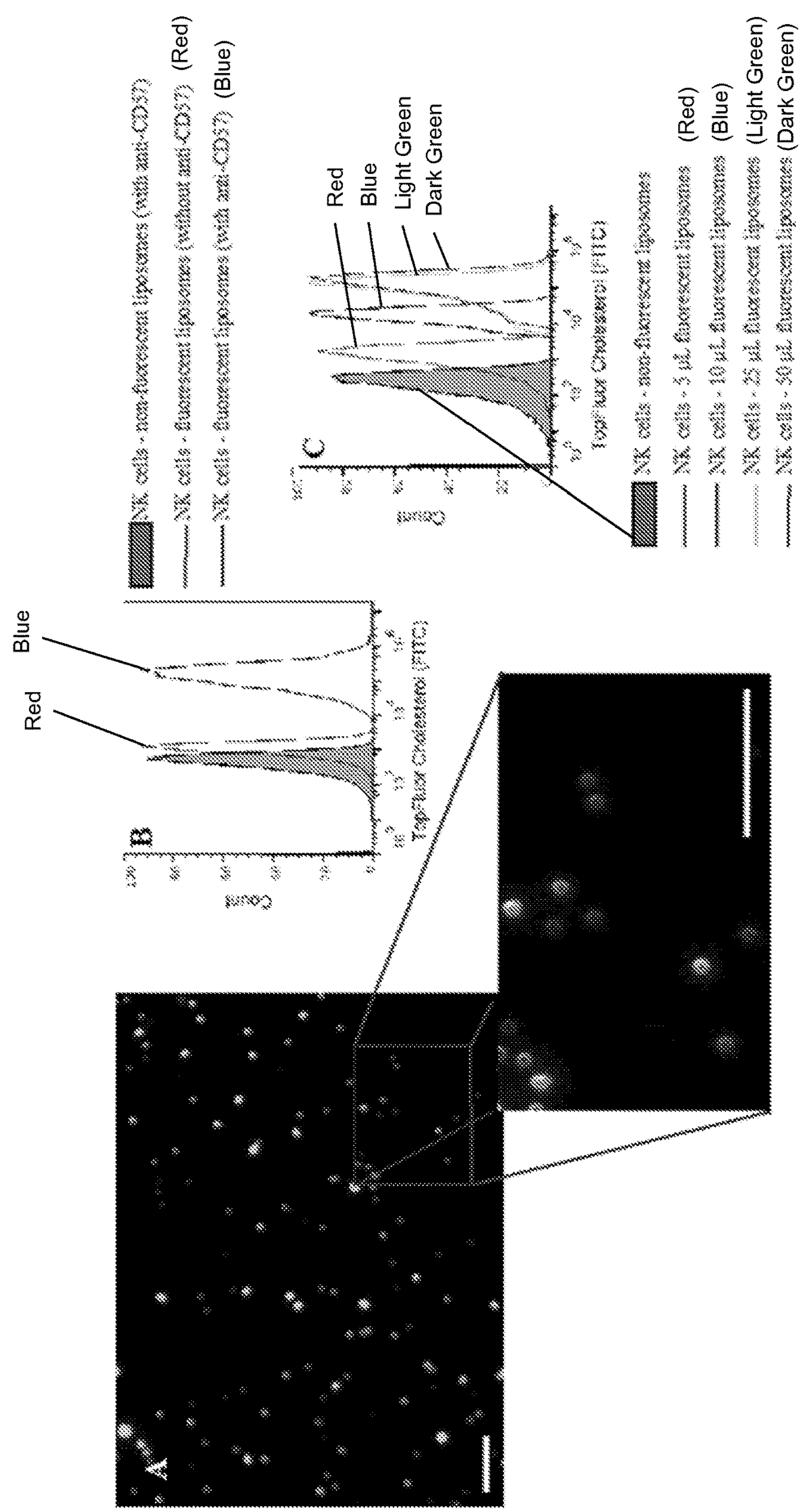
FIG. 15: (A.) NK cells conjugated to fluorescent liposomes with inset showing even distribution of liposomes on NK cell surface. (B.) Flow cytometry histogram indicating that conjugation is anti-CD57 dependent. (C.) Flow cytometry histograms showing the fluorescent shift intensity for different treatment volume of liposomes. Scale bar=100 nm.

Anti-CD57 on the liposome surface mediates conjugation of liposome to NK cells. Conjugation of TRAIL-functionalized liposomes to NK cells is mediated by CD57 expressed on the surface of NK cells and anti-CD57 functionalized on the liposome surface (FIG. 14C). Conjugating TRAIL-functionalized liposomes to NK cells did not cause any detrimental effects on NK cells (FIGS. 20C and 20D). It has been shown that long-circulating liposomes can effectively target solid tumors in cancer patients. Conjugating liposomes to NK cells can further increase the circulating time, which is an important criterion for targeted drug delivery. Additionally, since the natural niche of NK cells is lymph nodes, conjugating therapeutic liposomes to NK cells can specifically target micrometastases in the lymph nodes. To ensure successful conjugation of TRAIL-functionalized liposomes to NK cells, liposomes composed of fluorescent TopFluor cholesterol were used. Fluorescent images indicated that liposomes were successfully conjugated to NK cells (FIG. 15A). Closer examination indicated that liposomes were evenly coated on the surface of NK cells (FIG. 15A inset). Flow cytometric analysis revealed that NK cells conjugated to fluorescent liposomes functionalized with anti-CD57 showed a shift in fluorescent intensity peak with respect to NK cells conjugated to non-fluorescent liposomes (FIG. 15B). To investigate any non-specific interaction of liposomes with NK cells, NK cells were incubated with fluorescent liposomes without functionalized anti-CD57. Fluorescent intensity peak showed a small shift with respect to the control, indicating that there was minimal non-specific interaction. Functionalizing more PEG on the liposome surface could further reduce non-specific interactions. To determine the volume of liposomes needed to completely saturate the CD57 receptors on NK cells, $1\times10^6$ NK cells were incubated with different volumes of fluorescent liposomes. Flow cytometry histograms indicated increasing shift in fluorescent intensity peak for increasing volume of liposomes. For a treatment volume of 25 μL and 50 μL, there was no change in fluorescent intensity peak, indicating that a treatment volume of 25 μL saturated all the available CD57 receptors on the surface of NK cells (FIG. 15C).

Figure 16:
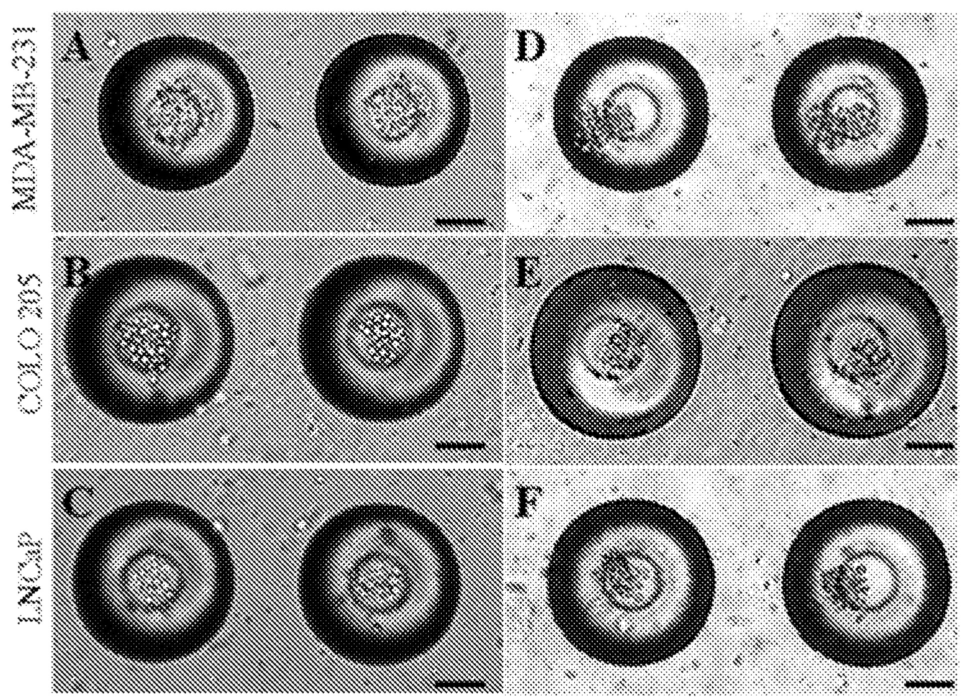
FIG. 16: (A.) MDA-MB-231, (B.) COLO 205 and (C.) LNCaP cells seeded in MB arrays immediately after seeding and 24 hr after seeding (D-F). Scale bar=100 μm.

Cancer cell lines cultured in microbubbles form small micrometastasis-like spheroids. Micrometastases are small aggregates of cancer cells less than 2 mm in diameter and they can remain dormant for many years before forming overt metastases. Microfabrication has led to the development of 3D cell culture systems which have taken cancer cell lines a step closer to in vivo tumors. A model for micrometastasis should be able to recapitulate the in vivo microenvironment. Microenvironment plays an important role in driving cells in micrometastasis progressively towards becoming an established metastatic lesion ultimately leading to secondary metastases5. We have shown that MB arrays can concentrate soluble factors secreted by cells to create a microenvironmental niche for cells cultured in them47. Cancer cells seeded in MB arrays form micrometastasis-like aggregates 24 hr after culture (FIG. 16). We seeded MDA-MB-231 (FIG. 16A), COLO205 (FIG. 16B) and LNCaP (FIG. 16C) cells at similar seeding density and observed the formation of micrometastasis-like aggregates after 24 hr in culture (FIG. 16D-4F).

Figure 17:
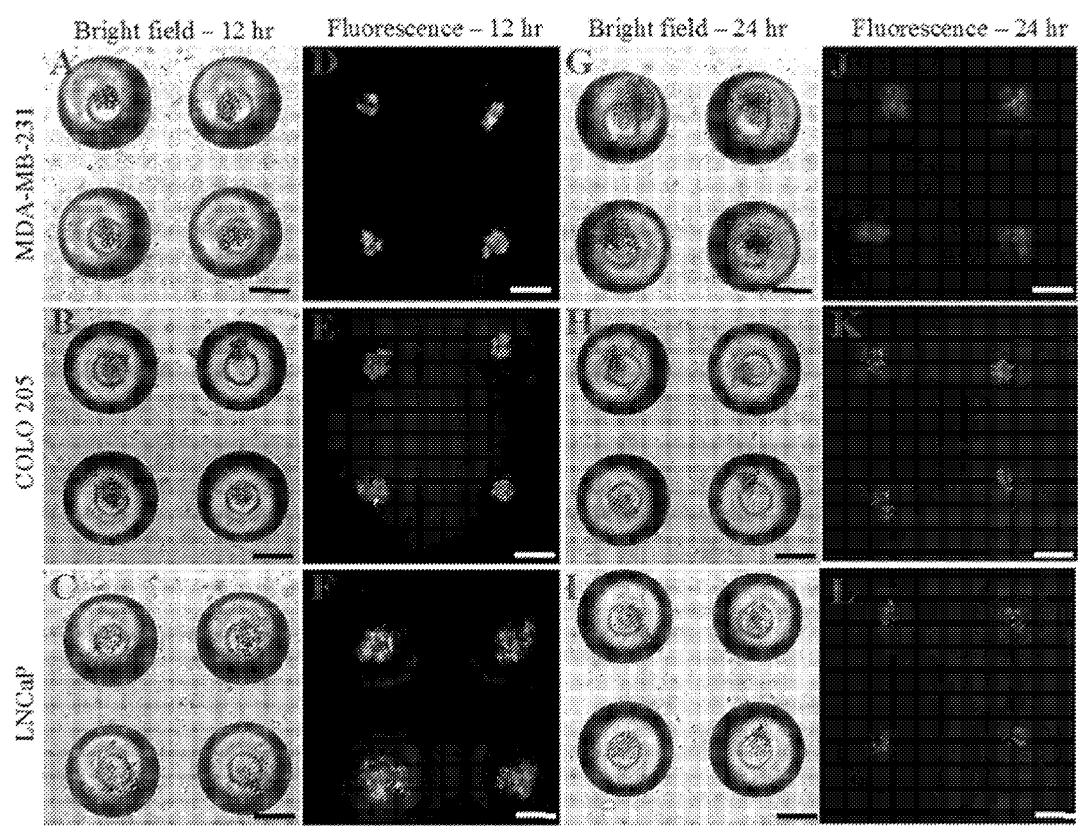
FIG. 17: Bright field (A-C, G-I) and fluorescent (D-F, J-L) images of MDA-MB-231, COLO 205 and LNCaP cells labelled with Annexin-V FITC (green, seen as bright in black & white) and propidium iodide at 12 hr (A-F) and 24 h (G-L) respectively. Scale bar=100 μm.
Figure 18:
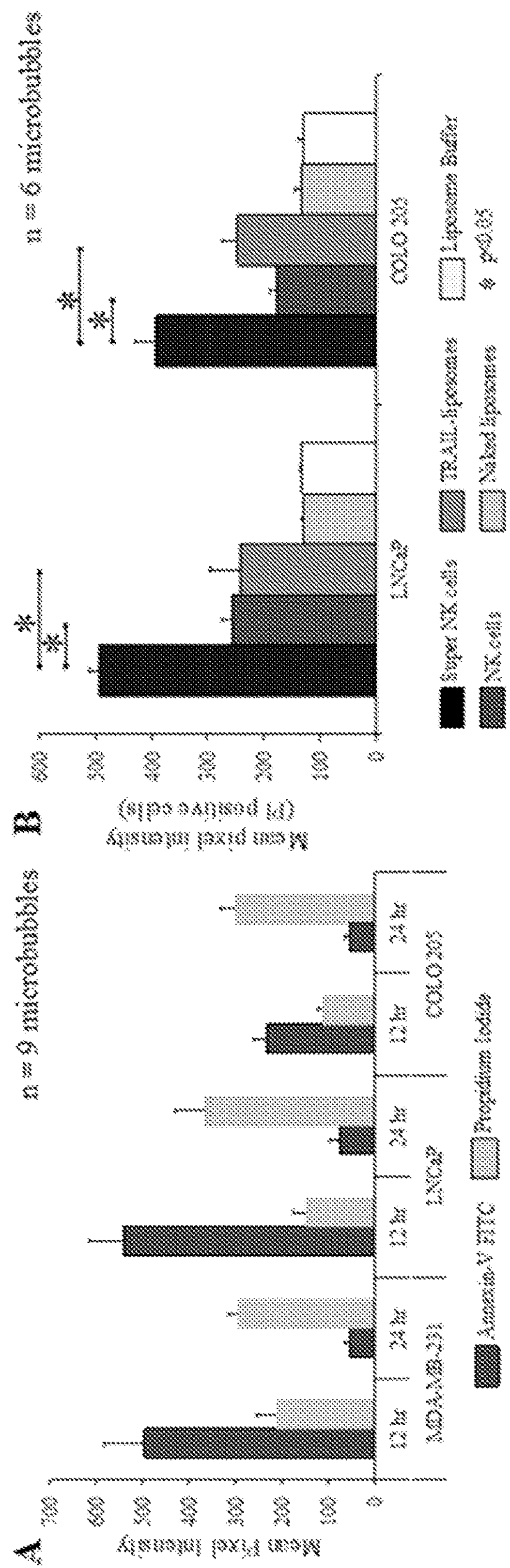
FIG. 18: Bar graphs of mean pixel intensity of (A.) Annexin-V FITC and PI positive cells by the end of 12 hr and 24 hr (B.) PI positive cells for different culture conditions by the end of 24 hr.
Figure 21:
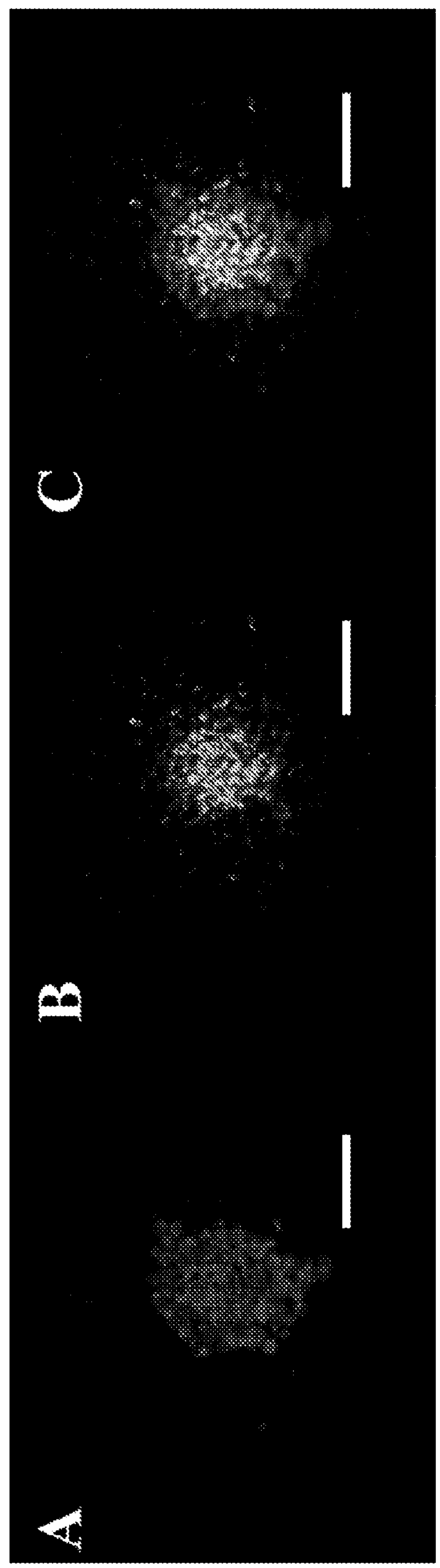
FIG. 21. Confocal micrographs of (A) LNCaP cells, (B) super NK cells and (C) LNCaP (red, seen as dull grey in black & white) and super NK cells (green, seen as bright in black & white) cells seeded in a single MB. Scale bar=100 μm FIG. 22. Flow cytometry histograms indicating the expression of death receptors in the cancer cell lines used in Example 2. The shift in fluorescent intensity indicates the amount of expression of DR4 (red) and DR5 (blue) on the surface of cancer cells.
Figure 22:
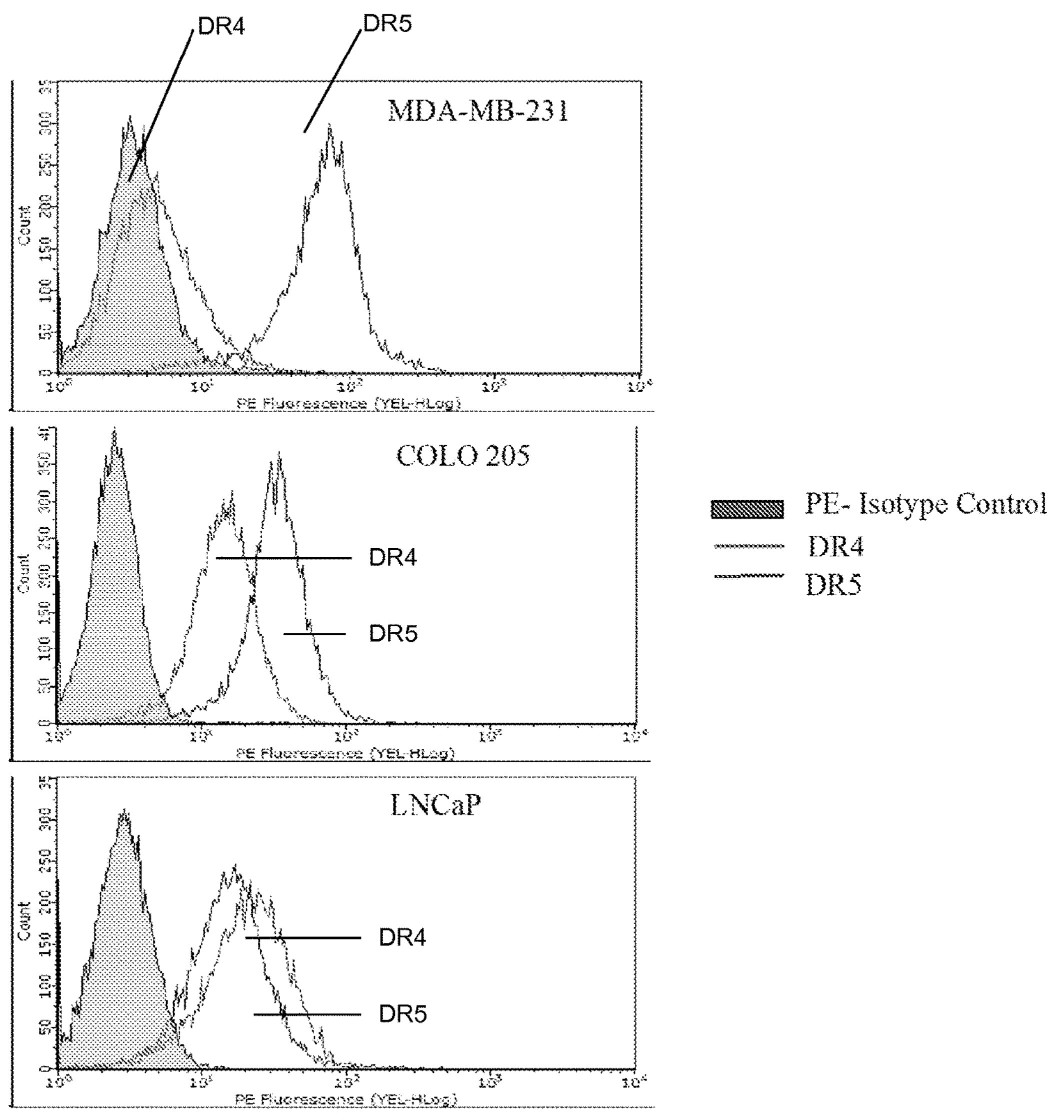
Figure 23:
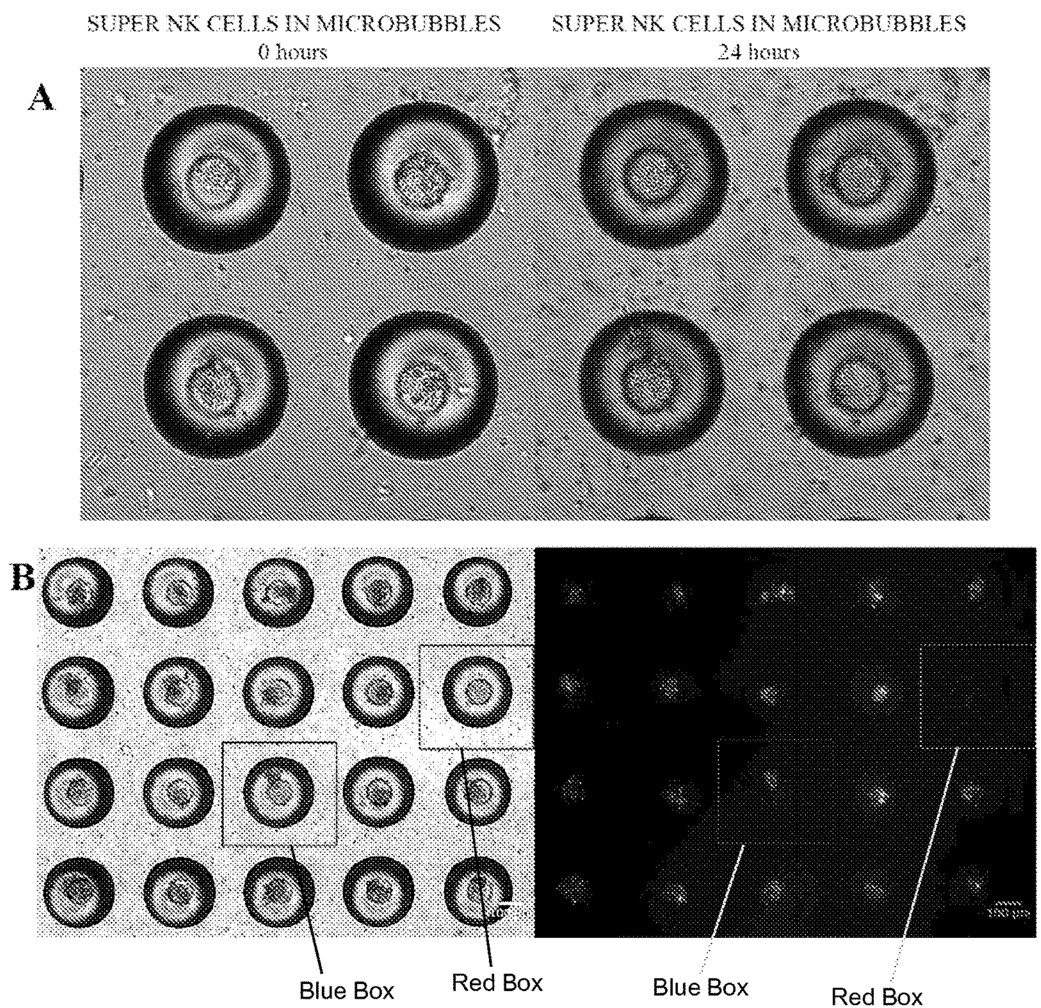
FIG. 23. A. Super NK cells cultured in MB arrays do not form aggregates unlike when they are cultured with cancer cells. They mostly remain as single cells 24 hours after culture. B. Cells that stained positive for Annexin-V FITC and PI are cancer cells and not super NK cells as evidenced by the bright field and fluorescent images that indicate that in MB well without cancer cells (red box) there is no signal for either Annexin-V FITC or PI from that particular MB. In MB wells where cancer cells from separate aggregates (blue box) it is evident that cancer cells stain positive for Annexin-V FITC and PI and not the super NK cells.
Figure 24:
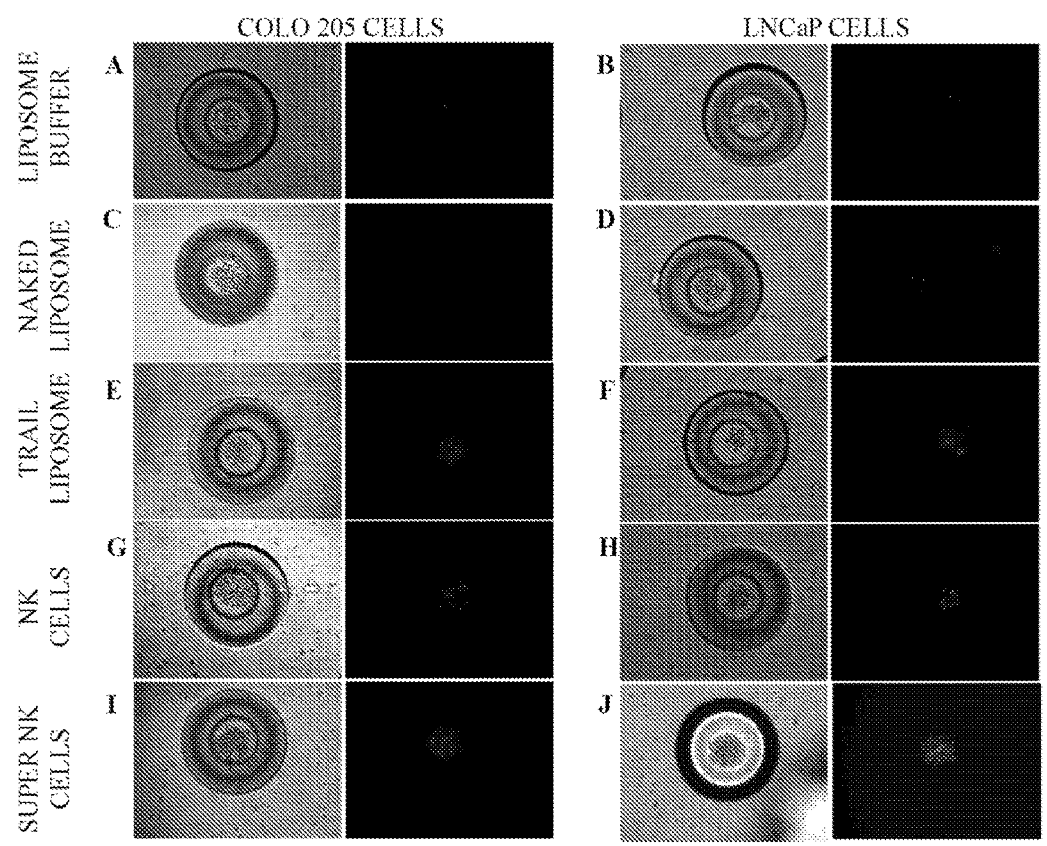
FIG. 24. Bright field and fluorescent images of MB stained with PI after 24 hours in culture. MB that were incubated with liposome buffer, naked liposomes, TRAIL functionalized liposomes, NK cells or super cells prior to seeding cancer cells (COLO 205, LNCaP).

Cancer cells progressively become apoptotic when cultured with super NK cells in MB. To determine the effectiveness of super NK cells in targeting cancer cells, super NK cells were seeded prior to seeding cancer cells first in MB arrays. Confocal micrographs of LNCaP cells labelled with CellTracker red and super NK cells labelled with CellTracker green cultured in a single MB are shown in FIG. 21. The images shown are a superimposition of all the Z-plane images acquired with individual filters for LNCaP cells (FIG. 21A) and super NK cells (FIG. 21B), and both the channels to visualize the co-culture of LNCaP and super NK cells in a MB (FIG. 21C). The cell lines chosen for this study were based on reports suggesting that these cells readily metastasize to the lymph nodes in experimental animal models (MDA-MB-23159, COLO 20560 and LNCaP61). The cell lines were characterized for the expression of death receptors (DR4 and DR5). Flow cytometric analysis for surface expression of DR indicated that the three cell lines showed positive expression of death receptors (FIG. 22). TRAIL has been shown to induce apoptosis in cancer cells by binding to death receptors. TRAIL is a toxin that is involved in the body's natural defense mechanism that holds advantages over other chemotherapeutic drugs that can be toxic to non-cancerous cells62. The first step taken by cells undergoing apoptosis is the loss of membrane integrity, which leads to the exposure of phospholipids. Annexin-V based apoptosis detection assay exploits this loss of membrane integrity. Annexin-V binds to exposed phospholipids in cells undergoing apoptosis and is a marker for early stages of apoptosis63. Propidium iodide (PI) is a fluorescent membrane impermeable DNA binding stain that is a marker for dead cells those have completely lost membrane integrity63. Fluorescein isothiocyanate (FITC) conjugated Annexin-V and PI were used to label apoptotic and dead cells in situ in MB arrays seeded with cancer cells and super NK cells. We noticed that cancer cells were progressively driven towards apoptosis. After 12 hr of incubation of super NK cells with MDA-MB-231 (FIG. 17A), COLO205 (FIG. 17B) and LNCaP cells (FIG. 17C), most of the cells were positive for Annexin-V staining (green, seen as bright in black & white) and very few cells stained positive for PI (red, seen as dull grey in black & white) (FIG. 17D-5F), indicating that the cells were primarily in early stages of apoptosis. After 24 hr of incubation most of the cells formed a heterotypic aggregate and it was hard to distinguish between super NK cells and cancer cells (FIG. 17G-171). Super NK cells seeded in MB arrays without cancer cells did not form aggregates but mostly remained as individual cells even 24 hr after culture (FIG. 23A). By the end of 24 hr, cells were positive for PI (red, seen as dull grey in black & white), indicating that most of the cells were dead (FIG. 17J-17L). The mean pixel intensity for Annexin-V FITC and PI positive cells was quantified using ImageJ software and the bar graphs indicate that by 12 hr, most of the cells were positive for Annexin-V and by 24 hr, most of the cells were positive for PI (FIG. 18A). We conclude that cells that stained positively for Annexin-V and PI in co-cultured MB arrays were cancer cells since in a few MB where cancer cells formed a separate aggregate away from super NK cells, only cancer cell aggregates stained positive for Annexin-V and PI (FIG. 23B). Additionally, in MB arrays with only super NK cells there was no staining for either Annexin-V or FITC (FIG. 23B). MB arrays incubated with liposome buffer prior to cancer cell seeding (FIGS. 24A and 24B) were found to form healthy aggregates by the end of 24 hr and did not stain positive for PI. Naked liposomes were not able to induce apoptosis in cancer cells (FIGS. 24C and 24D) whereas liposomes functionalized with TRAIL were able to induce apoptosis in cancer cells (FIGS. 24E and 24F). NK cells were able to mediate apoptosis in cancer cells but the response was not significant (FIGS. 24G and 24H) in comparison to super NK cells (FIGS. 24I and 24J). The mean intensity for PI positive cells after 24 hr in culture indicates that super NK cells more significantly induced apoptosis in cancer cells in comparison to NK cells and TRAIL-functionalized liposomes (FIG. 18B).

Identification of disseminated tumor cells (DTCs) in lymph nodes has served as a prognosticator of poor survival in several types of cancers. The results from several clinical studies suggest that DTCs can remain inactive for several years before a patient is diagnosed with overt metastasis. This has led to the development of several targeted therapies to target micrometastases within a relatively short span of time. However, to date, an adaptive immune therapy based approach to amplify the therapeutic potential of endogenous NK cells has not been proposed. In this work we used microbubble arrays formed on PDMS as an in vitro model for mimicking lymph node micrometastases. We showed that lymph node-seeking cancer cells cultured with NK cells conjugated to TRAIL-functionalized liposomes in MB arrays begin to undergo apoptosis after 24 hr in culture. Our data indicates the usefulness of the present method for targeted therapies for cancer cells metastasizing to lymph nodes.

Example 3

This example provides another illustration of this disclosure where the intermediate cells are CD34+ hematopoietic stem and progenitor cells (HSPCs). The nanoparticles can be coated with (i.e., functionalized) anti-CD34 antibody and TRAIL. A composition comprising such nanoparticles can be administered as described herein. In the circulation, the liposomes will quickly attach to the surface of CD34+ HSPC, causing the HSPC to be coated with the therapeutic protein TRAIL. The TRAIL-coated HSPC will then "home" back to the bone marrow through the natural stem cell homing process. This phenomenon is well known and forms the basis for bone marrow transplant, in which HSPC are introduced intravenously to a bone marrow recipient, and then the HSPC find their way back to the bone marrow and engraft there. It may be advantageous to repeat with one additional liposome dose 24 hours after the first dose, as the stem cell homing process is gradual and is promoted by the reestablishment of the natural GCSF chemotactic gradient into the marrow (after exogenous GCSF is cleared from the system). Once in the bone marrow microenvironment, TRAIL-coated HSPC will come into close contact with dormant tumor cells residing in the bone marrow, and will induce apoptosis, programmed cell death, in the tumor cells. It is expected that the effects of the TRAIL protein will be transient: sufficient to induce apoptosis in bone-marrow-residing dormant tumor cells, but without any lasting effects on erythropoiesis.

To mobilize the HSPCs, the patient may be treated for several (such as up to 5, from 5-10 or more) days with granulocyte colony stimulating factor (GCSF), which is known to "mobilize" the HSPCs from the bone marrow into the peripheral circulation. GCSF is a natural peptide and a clinically approved drug, which is used to mobilize HSPC to the peripheral circulation. When the HSPCs are in the peripheral circulation, they can be harvested for directed functionalization, or the individual can be administered the nanoparticle composition.

The therapeutic molecule placed on the liposomes which becomes attached to the surface of HSPC does not have to be TRAIL, and can be any type of molecule that causes cancer cell death via surface contact interactions. The therapeutic molecule need not be attached to the HSPC via nanoscale liposomes functionalized with antibody, and could be attached via some other type of nano particle, or even a composite molecule with a therapeutic domain conjugated to an adhesion/attachment end. A feature of this embodiment is the sequential process of: (1) causing HSPC to leave the BM and enter into the peripheral circulation, (2) attachment of therapeutic molecule carrying nanoparticles to the HSPC surface while the HSPC are in the peripheral circulation, and (3) exploiting the natural tendency of HSPC to home back to the bone marrow, to carry the therapeutic molecule to the bone marrow and neutralize (dormant) tumor cells that are residing in the bone marrow.

Although the present invention has been described for the purpose of illustration, it is understood that such detail is solely for that purpose and variations can be made by those skilled in the art without departing from the spirit and scope of the invention which is defined by the following claims.

The invention claimed is:

1. A method of killing metastatic cancer cells comprising:

a) providing nanoparticles which are functionalized with antibodies to CD57 and therapeutic molecules selected from the group consisting of tumor necrosis factor-related apoptosis inducing ligand (TRAIL) and Fas ligand, wherein the antibodies to CD57 on the nanoparticles bind to CD57 on NK-1 cells in circulation, and wherein the TRAIL interacts with DR4 and DR5 receptors, and the Fas ligand interacts with Fas on cancer cells causing apoptosis of the cancer cells; and b) introducing the nanoparticles into the circulation of an individual in need of treatment thereby allowing the nanoparticles to bind to the NK-1 cells and the NK-1 cells to seek out cancer cells thereby causing the nanoparticles to interact with the cancer cells via the therapeutic molecules causing cell death of the cancer cells.

2. The method of claim 1, wherein the nanoparticles are liposomes.

3. The method of claim 2, wherein the liposomes are unilamellar liposomes, wherein majority of the liposomes have a size from 50 to 250 microns.

4. The method of claim 1, wherein the nanoparticles are introduced into the circulation of an individual by intravenous administration.

5. The method of claim 1, wherein the nanoparticles are introduced into the lymphatic circulation of the individual.

6. The method of claim 1, wherein the nanoparticles are introduced into the circulation of an individual prior to, after, or at the same time as surgical removal of a tumor.

7. The method of claim 1, comprising an additional step of administering an agent which enhances the killing effect of the therapeutic molecules on cancer cells.

8. A method of killing metastatic cancer cells that are residing in a lymph node comprising:

a) providing nanoparticles which are functionalized with antibodies to CD57 and therapeutic molecules selected from the group consisting of tumor necrosis factor-related apoptosis inducing ligand (TRAIL) and Fas ligand, wherein the antibodies to CD57 on the nanoparticles bind to CD57 on NK-1 cells in circulation, and wherein the TRAIL interacts with DR4 and DR5 receptors, and the Fas ligand interacts with Fas on cancer cells causing apoptosis of the cancer cells; and b) introducing the nanoparticles into the lymph circulation near the lymph node of an individual thereby allowing the nanoparticles to bind to the NK-1 cells and the NK-1 cells to seek out cancer cells thereby causing the nanoparticles to interact with the cancer cells residing in the lymph node and causing cell death of the cancer cells in the lymph node.

9. The method of claim 8, wherein the nanoparticles are liposomes.

10. The method of claim 9, wherein the liposomes are unilamellar liposomes, wherein majority of the liposomes have a size from 50 to 250 microns.

* * * * *